United States Patent
Satake et al.

(10) Patent No.: US 9,687,248 B2
(45) Date of Patent: Jun. 27, 2017

(54) ENDOSCOPE TREATMENT TOOL

(71) Applicant: OLYMPUS CORPORATION, Tokyo (JP)

(72) Inventors: Motoi Satake, Tokyo (JP); Kensuke Uesaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/751,814

(22) Filed: Jun. 26, 2015

(65) Prior Publication Data

US 2015/0374381 A1  Dec. 31, 2015

Related U.S. Application Data

(63) Continuation of application No. PCT/JP2014/061233, filed on Apr. 22, 2014.

(60) Provisional application No. 61/820,355, filed on May 7, 2013.

(51) Int. Cl.
  *A61B 17/128*   (2006.01)
  *A61B 17/122*   (2006.01)

(52) U.S. Cl.
  CPC ........ *A61B 17/1285* (2013.01); *A61B 17/122* (2013.01)

(58) Field of Classification Search
  CPC .................... A61B 17/1285; A61B 17/122
  See application file for complete search history.

(56) References Cited

U.S. PATENT DOCUMENTS

| 5,766,184 A | 6/1998 | Matsuno et al. |
| 7,727,247 B2 | 6/2010 | Kimura et al. |
| 2002/0128667 A1 | 9/2002 | Kobayashi et al. |

(Continued)

FOREIGN PATENT DOCUMENTS

| EP | 1 604 614 A1 | 12/2005 |
| EP | 2 098 176 A2 | 9/2009 |

(Continued)

OTHER PUBLICATIONS

International Search Report dated Jun. 24, 2014 issued in PCT/JP2014/061231.

(Continued)

*Primary Examiner* — Corrine McDermott
*Assistant Examiner* — Tin Nguyen
(74) *Attorney, Agent, or Firm* — Scully, Scott, Murphy & Presser, PC

(57) ABSTRACT

An endoscope treatment tool includes a clip main body which includes a pair of arm portions; a pressing tube through which the clip main body is inserted; a locking portion which is disposed on an inner circumferential surface of a proximal end of the pressing tube; a locked portion which is disposed on the proximal end side of the clip main body; a sheath portion; a linear member connected to the clip main body and inserted through the sheath portion; a stopper portion which is configured to regulate a protrusion length of the linear member with respect to the distal end of the sheath portion; and a connection member which is disposed at a distal end of the linear member such that a connection between the linear member and the clip main body is released by regulating a movement of the clip main body.

7 Claims, 18 Drawing Sheets

(56) References Cited

U.S. PATENT DOCUMENTS

| | | | |
|---|---|---|---|
| 2002/0177861 A1* | 11/2002 | Sugiyama | A61B 17/122 606/151 |
| 2005/0143767 A1 | 6/2005 | Kimura et al. | |
| 2008/0140089 A1 | 6/2008 | Kogiso et al. | |
| 2011/0054498 A1 | 3/2011 | Monassevitch et al. | |

FOREIGN PATENT DOCUMENTS

| | | |
|---|---|---|
| EP | 2 371 302 A1 | 10/2011 |
| JP | S62-170010 U | 10/1987 |
| JP | H08-280701 A | 10/1996 |
| JP | 2002-345830 A | 12/2002 |
| JP | 2002-355249 A | 12/2002 |
| JP | 2004-216058 A | 8/2004 |
| JP | 2007-097664 A | 4/2007 |
| JP | 2010-221059 A | 10/2010 |
| JP | 2012-065834 A | 4/2012 |
| WO | WO 2010/133215 A1 | 11/2010 |
| WO | 2012/039163 A1 | 3/2012 |

OTHER PUBLICATIONS

International Search Report dated Jun. 24, 2014 issued in PCT/JP2014/061260.
International Search Report dated Jun. 24, 2014 issued in PCT/JP2014/061233.
Office Action dated Jun. 27, 2016 in related U.S. Appl. No. 14/476,172.
Extended Supplementary European Search Report dated Nov. 18, 2016 in related European Patent Application No. 14 79 4408.6.
Extended Supplementary European Search Report dated Nov. 18, 2016 in related European Patent Application No. 14 79 4117.3.
Extended Supplementary European Search Report dated Nov. 18, 2016 in related European Patent Application No. 14 79 5099.2.
Office Action dated Apr. 3, 2017 received in U.S. Appl. No. 14/476,132.

* cited by examiner

ENDOSCOPE TREATMENT TOOL

This application is a continuation application based on a PCT International Application No. PCT/JP2014/061233, filed on Apr. 22, 2014, whose priority is claimed on U.S. Provisional Patent Application No. 61/820,355, filed on May 7, 2013. The content of the PCT International Application and the US Provisional Patent Application are incorporated herein by reference.

BACKGROUND OF THE INVENTION

Field of the Invention

The present invention relates to an endoscope treatment tool inserted into a body and used to ligate a tissue.

Description of Related Art

Endoscope treatment tools which are ligation devices including clip units used to ligate openings formed in tissues or blood vessels have been used. As such an endoscope treatment tool, for example, an endoscope treatment tool disclosed in Japanese Unexamined Patent Application, First Publication No. 2010-221059 has been known.

The endoscope treatment tool disclosed in Japanese Unexamined Patent Application, First Publication No. 2010-221059 includes a clip unit and an endoscope ligation device to introduce the clip unit into a body. The clip unit is configured to include a claw, a pressing tube, and a connection plate. The claw is a portion in which a halfway portion is bent in an a shape and both ends thereof are formed in a claw shape. An arm portion of the claw is configured to be opened slightly by elastic resilience of the arm portion of the claw in a released natural state.

In the connection plate, a hole is provided in a hand-side end portion and a hook portion is formed in a distal-end-side end portion. The hook portion is hooked to a proximal-end-side loop portion of the claw so as to be disposed inside the pressing tube. At this time, the α portion of the claw is not drawn deeply into the pressing tube and the arm portion of the claw can be opened slightly.

The endoscope ligation device includes an introduction tube, a manipulation wire (linear member), a manipulation portion main body, and a slider. A coil sheath is inserted so as to be advanceable and retractable inside the introduction tube. The manipulation wire is inserted so as to be advanceable and retractable inside the coil sheath. The manipulation portion main body is attached to the proximal end of the coil sheath. The slider is configured to be attached to the proximal end of the manipulation wire via a pipe and to be slidable with the manipulation portion main body. The above-described clip unit is attached to the distal end of the manipulation wire.

A halfway portion of the manipulation wire is turned back through the hole of the connection plate. Portions on both sides of the manipulation wire formed as two wires by turning back the halfway portion are inserted parallel to each other so as to be advanceable and retractable inside the coil sheath. The slider is fixed on the both proximal ends of the manipulation wire. The pipe is fitted to the both proximal ends of the manipulation wire.

The endoscope treatment tool having the above-described configuration disclosed in Japanese Unexamined Patent Application, First Publication No. 2010-221059 is used as follows.

The clip unit is accommodated inside the introduction tube. The introduction tube of the endoscope ligation device in this state is inserted into a channel of an endoscope which has been inserted into a body cavity in advance. After the distal end of the introduction tube reaches inside the body cavity, the introduction tube is pulled toward the hand side to make the clip unit to protrude from the distal end of the introduction tube.

By pulling the slider toward the hand side with a light force, the α portion of the claw is drawn inside the pressing tube to open the claw more widely. In this state, the introduction tube is pushed into the endoscope to press the opened claw against a target bleeding site or the like inside a body cavity.

In this state, when the slider is strongly pulled toward the hand side, the proximal end of the arm portion is drawn to the pressing tube so that the claw is closed and the tissue of the bleeding site is grasped. When the slider is pulled more strongly, the hook portion of the connection plate is stretched so that the clip unit is separated from the endoscope ligation device and detained inside the body cavity while the clip unit grasping the tissue.

SUMMARY OF THE INVENTION

According to a first aspect of the present invention, an endoscope treatment tool includes a clip main body which includes a pair of arm portions, each of the pair of the arm portions extending from a proximal end to a distal end and facing each other; a pressing tube through which the clip main body is inserted and is provided to make the distal ends of the pair of the arm portions approach each other; a locking portion which is disposed on an inner circumferential surface of a proximal end of the pressing tube; a locked portion which is disposed on the proximal end side of the clip main body; a sheath portion of which the clip main body is disposed at a distal end side; a linear member connected to the clip main body and inserted through the sheath portion to be capable of being advanced and retracted from the distal end of the sheath; a stopper portion which is configured to regulate a protrusion length of the linear member with respect to the distal end of the sheath portion; and a connection member which is disposed at a distal end of the linear member such that a connection between the linear member and the clip main body is released by regulating a movement of the clip main body, in a state in which the locked portion is positioned more proximal beyond the locking portion to be positioned on a proximal end portion side at the outside of the pressing tube when the linear member is protruded at a maximum protrusion length allowed.

According to a second aspect of the present invention, in the endoscope treatment tool according to the first aspect, the connection member may include a hook portion which engages with the clip main body, and in the state in which the connection member is positioned inside the pressing tube, a relative movement in a radial direction between the clip main body and the hook portion may be regulated by the pressing tube such that release of the engagement between the hook portion and the clip main body is prevented.

According to a third aspect of the present invention, in the endoscope treatment tool according to the second aspect, the sheath portion may include a support member which is capable of accommodating the proximal end of the pressing tube in a distal side of the support member, and in a state in which the clip main body is accommodated in the pressing tube such that the locked portion is positioned more distal than the locking portion, when the linear member is protruded at a maximum protrusion length allowed by the stopper portion, at least part of the proximal part of the pressing tube may be accommodated in the support member.

According to a fourth aspect of the present invention, in the endoscope treatment tool according to the third aspect, the stopper portion may be disposed at the distal end side of the sheath portion.

According to a fifth aspect of the present invention, in the endoscope treatment tool according to the fourth aspect, the connection member may be connected to a proximal end of the clip main body, and in a state in which the clip main body is moved such that the locked portion is positioned more proximal than the locking portion, the proximal end of the clip main body may be protruded from the proximal end portion of the pressing tube such that the connection member is positioned outside the pressing tube to release the connection.

According to a sixth aspect of the present invention, in the endoscope treatment tool according to the fifth aspect, the hook portion may be connected to the linear member and may be capable of rotating around an axial which is perpendicular to a longitudinal axis of the linear member.

DETAILED DESCRIPTION OF THE INVENTION

Hereinafter, an embodiment of an endoscope treatment tool according to the present invention will be described with reference to FIGS. 1 to 25. Throughout all of the drawings, ratios of the thicknesses or dimensions of respective constituent elements are appropriately adjusted for clarity.

Figure 1:
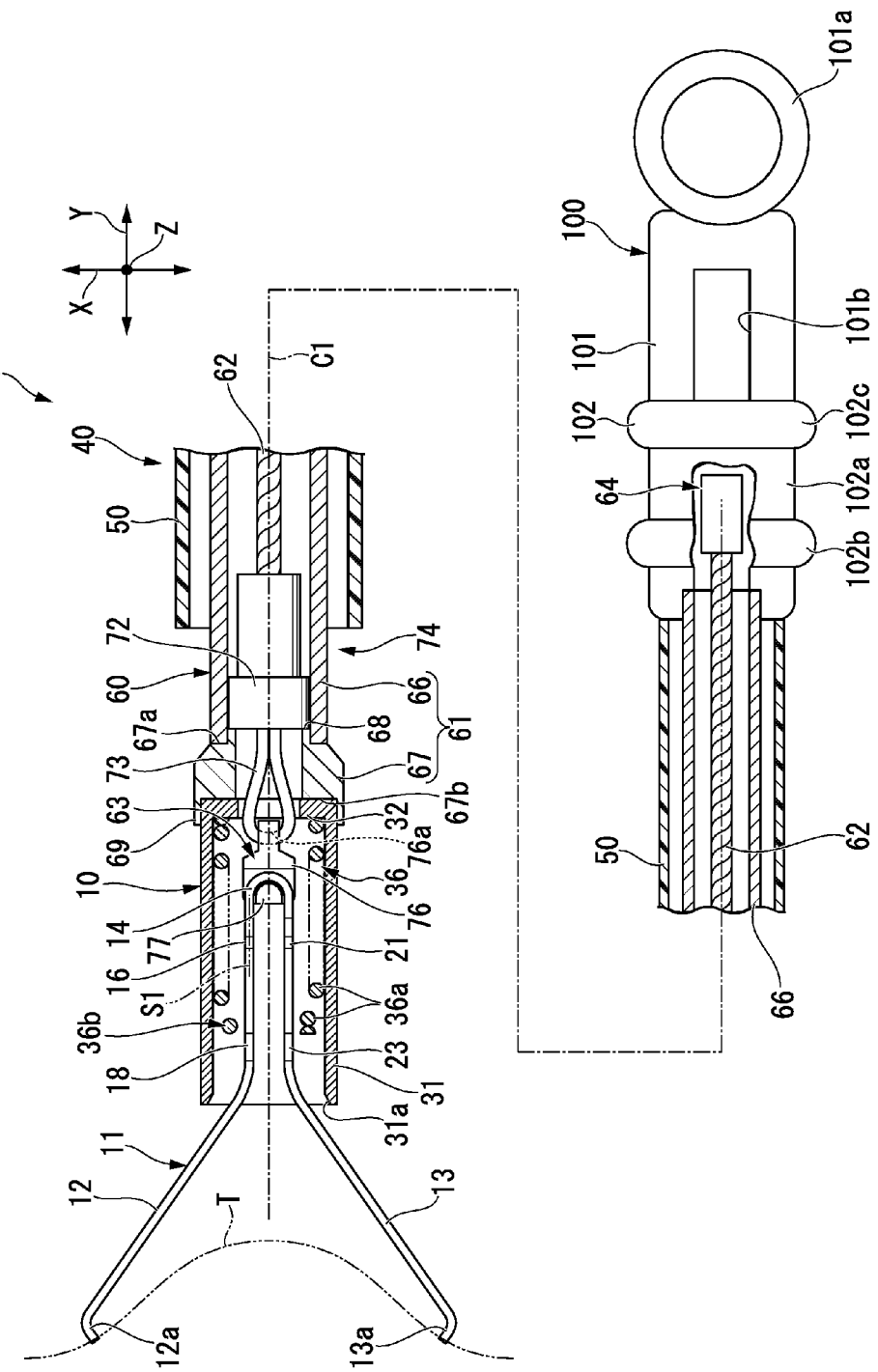
FIG. 1 is a sectional view schematically showing an endoscope treatment tool in which a clip unit according to an embodiment of the present invention is used by cutting away a part of a side surface of the endoscope treatment tool.
Figure 2:
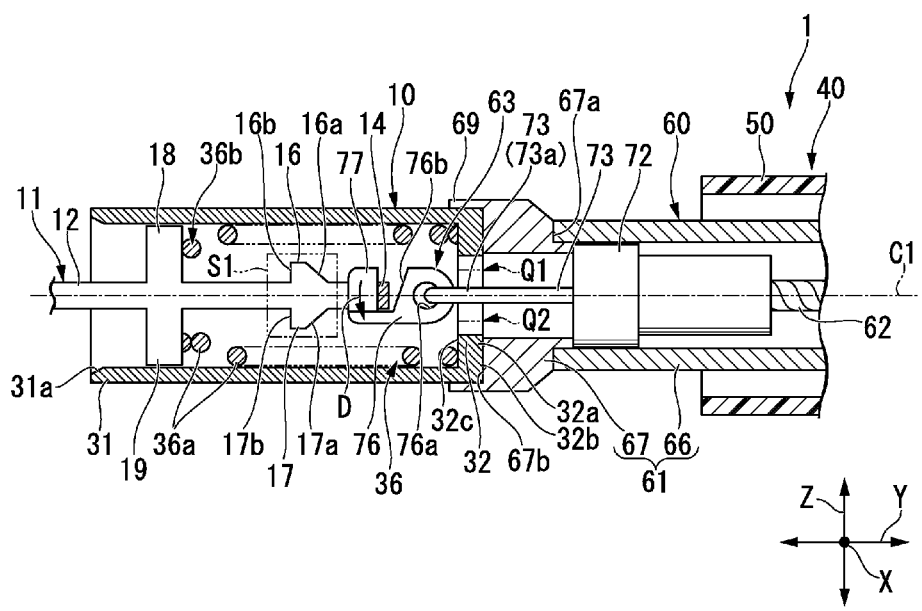
FIG. 2 is a top sectional view schematically showing the distal end of the endoscope treatment tool in FIG. 1.

As shown in FIGS. 1 and 2, a ligation device as an endoscope treatment tool 1 includes a clip unit (hereinafter also abbreviated as a "clip") 10 and a treatment tool body 40. The clip 10 can be detachably mounted on a distal end of the treatment tool body 40. FIGS. 1 and 2 are top sectional views passing through an axial line C1 of a pressing tube 31 to be described below.

Figure 3:
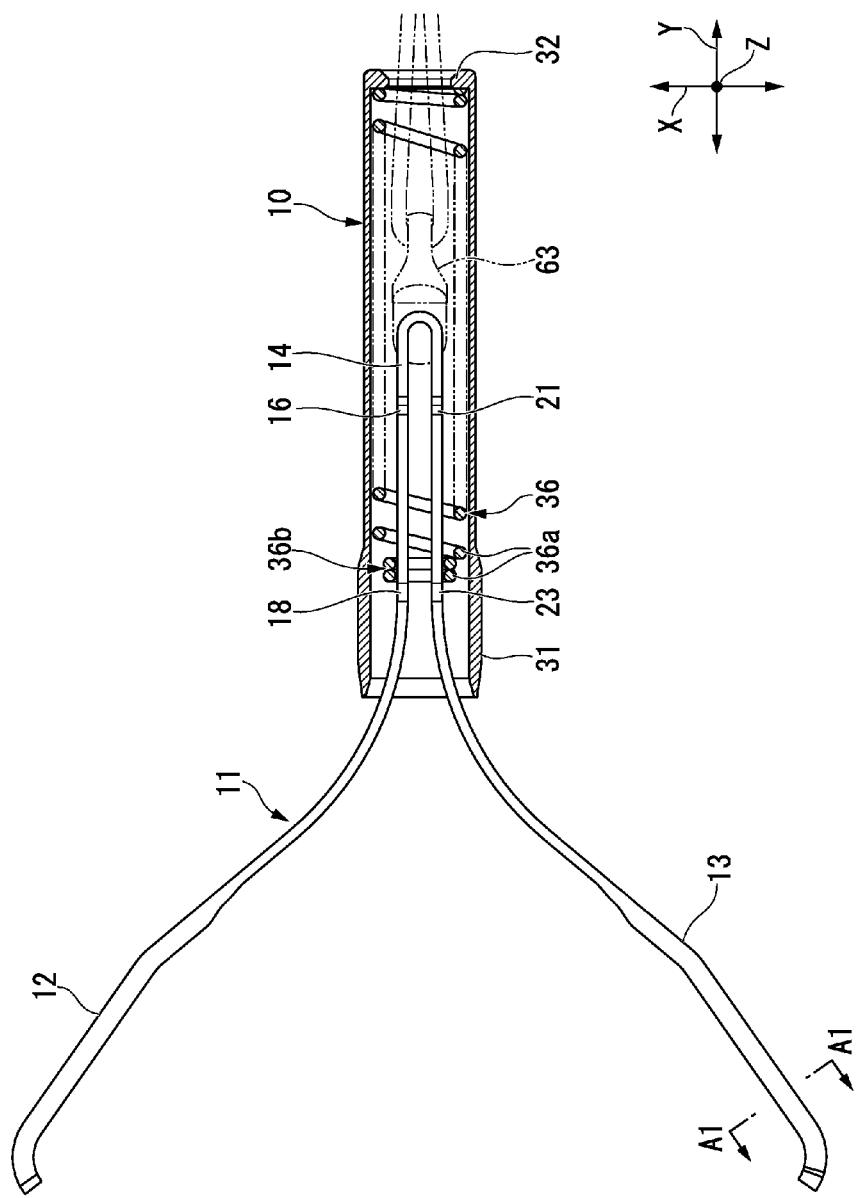
FIG. 3 is a side sectional view showing a clip unit in FIG. 1.
Figure 4:
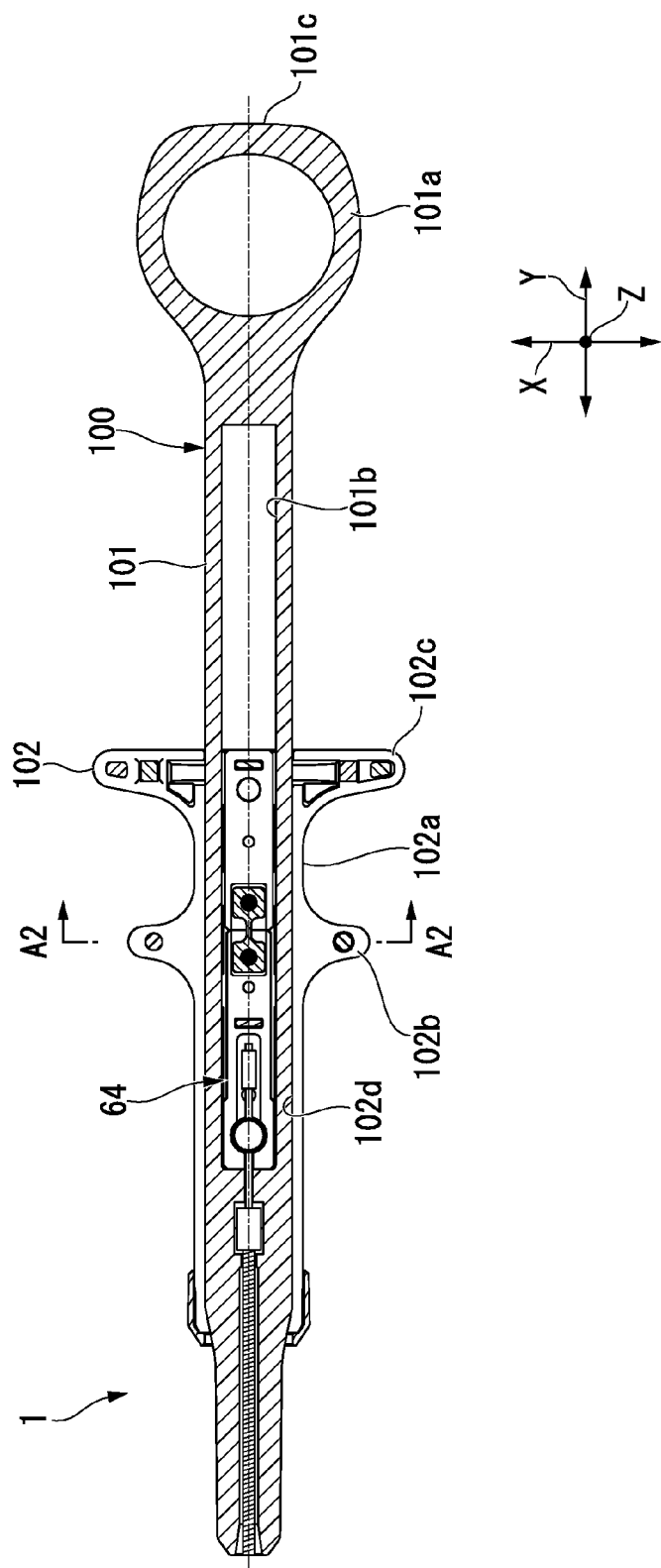
FIG. 4 is a side sectional view showing the proximal end of the endoscope treatment tool in FIG. 1.
Figure 5:
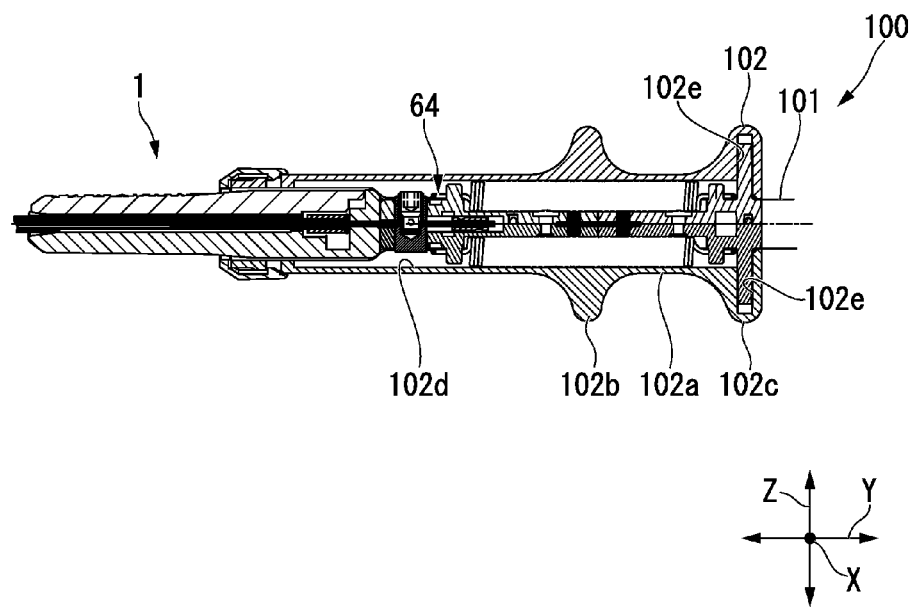
FIG. 5 is a top sectional view showing the proximal end of the endoscope treatment tool in FIG. 1.

FIG. 3 is a side sectional view showing the clip 10 of the endoscope treatment tool 1. FIG. 4 is a side sectional view showing a proximal end of the endoscope treatment tool 1. FIG. 5 is a top sectional view showing the proximal end of the endoscope treatment tool 1. Hereinafter, configurations and operations will be described with reference to the schematic drawings and main portions will be described with reference to the detailed drawings.

(Configuration: Arm Portions 12 and 13 of the Clip 10)

As shown in FIGS. 1 and 2, the clip 10 includes a clip main body 11, the pressing tube 31, and a helical spring (elastic member) 36. The pressing tube 31 is formed in a cylindrical shape and accommodates the proximal end of the clip main body 11. The helical spring 36 is accommodated inside the pressing tube 31. The members forming the clip 10 in addition to the clip main body 11 are formed of a material such as a cobalt-chromium alloy, titanium, or stainless steel. The clip 10 is configured to be capable of being observed by MRI (Magnetic Resonance Imaging) radioscopy.

The clip main body 11 includes a first arm portion 12, a second arm portion 13, and a middle portion 14. The first arm portion 12 and the second arm portion 13 are disposed to extend from the proximal end side to the distal end side of the clip main body 11 and face each other. The middle portion 14 is disposed to be located between a proximal end of the first arm portion 12 and a proximal end of the second arm portion 13.

The first arm portion 12 and the second arm portion 13 are formed to be mutually separated in a natural state from the proximal end side to the distal end side. A claw 12*a* extending toward a side of the second arm portion 13 is formed at a distal end of the first arm portion 12.

Figure 6:
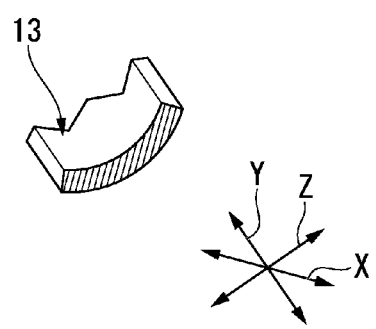
FIG. 6 is a schematic perspective view taken along the cutting line A1-A1 in FIG. 3.

In the first arm portion 12 and the second arm portion 13, a cross-sectional shape orthogonal to a longitudinal direction on the distal end side thereof is formed as an arc-like round shape, as shown in FIG. 6. More specifically, a middle portion of the outside surface of each of the arm portions 12 and 13 in an orthogonal direction Z to be described below is formed in a curved shape that is convex toward the outside.

Thus, for the first arm portion 12 and the second arm portion 13, the strength against bending is improved and frictional resistance to a sheath tube 50 to be described below is reduced, so that advancement and retraction operations can smoothly be performed.

(Configuration: First Locked Portions 16 and 17 of Clip 10)

Here, as shown in FIG. 1, an opposite direction X in which the first arm portion 12 and the second arm portion 13 face each other, an axial line direction Y parallel to an axial line C1 of the pressing tube 31, and the orthogonal direction Z orthogonal to each of the opposite direction X and the axial line direction Y are regulated. As shown in FIG. 2, two first locked portions 16 and 17 are provided at the proximal end of the first arm portion 12. The first locked portions 16 and 17 are provided to protrude from a lateral surface of the first arm portion 12 in the orthogonal direction Z on a criterion plane S1 parallel to the axial line (central axial line) C1 of the pressing tube 31. The first locked portions 16 and 17 protrude in opposite directions.

FIG. 2 is a diagram of the endoscope treatment tool 1 in FIG. 1 when viewed in a direction orthogonal to the criterion plane S1. In the top view shown in FIG. 2, the first locked portions 16 and 17 are formed to be line-symmetric with respect to the axial line C1.

As shown in FIG. 2, a proximal end surface 16*a* of the first locked portion 16 is formed to be separated and inclined from the first arm portion 12 (central axial line C1) toward the distal end side of the first locked portion 16. A distal end surface 16*b* of the first locked portion 16 is orthogonal to the axial line direction Y. A proximal end surface 17*a* and a distal end surface 17*b* of the first locked portion 17 are formed to be line-symmetric to the proximal end surface 16*a* and the distal end surface 16*b* of the first locked portion 16 with respect to the axial line C1, respectively.

(Configuration: Protrusion Portions 18 and 19 of Clip 10)

As shown in FIGS. 1 and 2, two protrusion portions 18 and 19 are provided more distal than the first locked portions 16 and 17 in the first arm portion 12. The protrusion portions 18 and 19 protrude from the lateral surface of the first arm portion 12 in the orthogonal direction Z. The protrusion portions 18 and 19 are formed to be line-symmetric with respect to the axial line C1 in a top view. Lengths of the protrusion portions 18 and 19 protruding from the first arm portion 12 in the orthogonal direction Z are longer than the first locked portions 16 and 17 which protrude from the first arm portion 12 in the orthogonal direction Z.

(Configuration: Arm Portion 13 of Clip 10)

As shown in FIG. 1, a claw 13*a* extending toward the side of the first arm portion 12 is formed at a distal end of the second arm portion 13.

Figure 7:
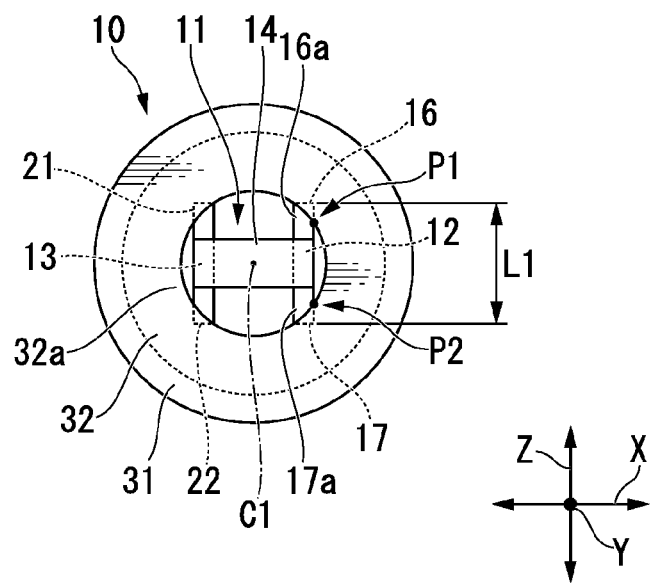
FIG. 7 is a diagram schematically showing a state of the clip unit in FIG. 1 when viewed from the proximal end side.
Figure 8:
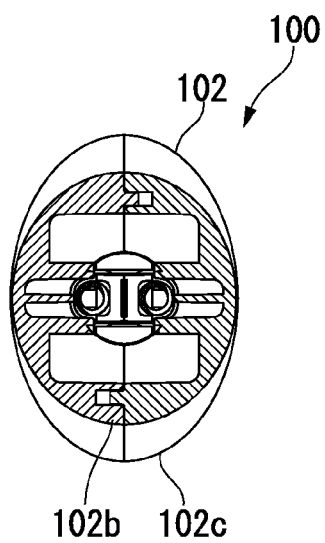
FIG. 8 is a diagram taken along the cutting line A2-A2 in FIG. 4.

In the second arm portion 13, second locked portions 21, 22 and protrusion portions 23, 24 are formed like the first locked portions 16, 17 and the protrusion portions 18, 19 of the first arm portion 12, respectively (the second locked portion 22 is referred to FIG. 7 and the protrusion portion 24 is not shown). That is, the second locked portions 21 and 22 protrude from the lateral surface of the second arm portion 13 in the orthogonal direction Z which is a direction away from the second arm portion 13. The protrusion portions 23 and 24 are provided to protrude from the lateral surface of the second arm portion 13 in the orthogonal direction Z more distal than the second locked portions 21 and 22 in the second arm portion 13. The second locked portions 21, 22 and the protrusion portions 23, 24 are disposed to be parallel to the first locked portions 16, 17 and the protrusion portions 18, 19 in the opposite direction X, respectively. That is, in a top view shown in FIG. 2, the second locked portions 21 and 22 overlap the first locked portions 16 and 17 and the protrusion portions 23 and 24 overlap the protrusion portions 18 and 19.

In a side view shown in FIG. 1, the first arm portion 12 and the second arm portion 13 are formed at positions which are line-symmetric with respect to the axial line C1.

For the clip main body 11, a plate formed of a cobalt-chromium alloy or the like is punched in a shape in which the arm portions 12 and 13, the middle portion 14, the first locked portions 16 and 17, the second locked portions 21 and 22, and the protrusion portions 18, 19, 23, and 24 are spread in a planar form. Then, the punched member is integrally formed in a C shape in a side view by bending a connection portion of the first arm portion 12 and the middle portion 14 and a connection portion of the second arm portion 13 and the middle portion 14.

(Configuration: Locking Portion 32 of Clip 10)

As shown in FIGS. 2 and 7, on the inner circumferential surface of the proximal end of the pressing tube 31, a locking portion 32 protrudes over the entire inner circumference surface. When viewed in the axial line direction Y shown in FIG. 7, an edge 32*a* of the locking portion 32 on a side of the axial line C1 is formed in a circular shape that is coaxial with the pressing tube 31. As shown in FIG. 2, a proximal end surface 32*b* (proximal-end-side end surface) and a distal end surface 32*c* (distal-end-side end surface) of the locking portion 32 are orthogonal to the axial line direction Y.

Portions on the proximal end side of the protrusion portions 18 and 19 in the first arm portion 12, portions on the proximal end side of the protrusion portions 23 and 24 in the second arm portion 13, and the middle portion 14 can be inserted into the locking portion 32. As shown in FIG. 7, a length L1 between an end of the first locked portion 16 and an end of the first locked portion 17 in the orthogonal direction Z is less than the inner diameter of the locking portion 32. In an initial state to be described below, parts of the first locked portions 16 and 17 are set to overlap the locking portion 32 when viewed in the axial line direction Y. That is, in the state shown in FIG. 7, the edge 32*a* is set such that the length L1 of the first locked portions 16 and 17 is longer than a height (a length of a line segment binding positions P1 and P2 in FIG. 7) of the edge 32*a* in which the first locked portions 16 and 17 face each other at the positions P1 and P2 in the orthogonal direction Z.

As shown in FIG. 2, a tapered surface 31*a* is formed over the entire inner circumference surface at the distal end of the pressing tube 31. The diameter of the tapered surface 31*a* expands toward the distal end side of the pressing tube. The pressing tube 31 and the locking portion 32 are integrally formed of a material such as a 64 titanium alloy (Ti-6AL-4V) or a cobalt-chromium alloy.

(Configuration: Helical Spring 36 of Clip 10)

As shown in FIG. 3, an end turn portion 36*b* is provided at the distal end of the helical spring 36. The inner diameter of the formed end turn portion 36*b* is less than that of the other portions of the helical spring 36.

When the helical spring 36 is accommodated inside the pressing tube 31, the distal end thereof locks with the protrusion portions 18, 19, 23, and 24 and the proximal end thereof locks with the locking portion 32. The proximal end of the helical spring 36 and the locking portion 32 may be fixed by welding or the like.

The portions on the proximal end side of the protrusion portions 18 and 19 in the first arm portion 12, the portions on the proximal end side of the protrusion portions 23 and 24 in the second arm portion 13, and the middle portion 14 can be inserted into the helical spring 36. When the protrusion portions 18, 19, 23, and 24 are moved toward the proximal end side, the protrusion portions 18, 19, 23, and 24 lock with the end turn portion 36b of the helical spring 36. Even when the helical spring 36 does not include the end turn portion 36b, the same advantage can be obtained by using a separate member such as a washer at the distal end of the helical spring 36.

In the initial state of the clip 10 shown in FIGS. 1 and 2, the proximal end of the first arm portion 12, the proximal end of the second arm portion 13, and the middle portion 14 are accommodated on the distal end side with respect to the locking portion 32 inside the pressing tube 31. The first locked portions 16 and 17 and the second locked portions 21 and 22 do not come into contact with the locking portion 32 of the pressing tube 31. Wires 36a of the helical spring 36 adjacent to each other in the axial line direction Y are separated from each other. The helical spring 36 is compressed in the axial line direction Y slightly more than in the natural state. The distal end of the first arm portion 12 and the distal end of the second arm portion 13 of the clip main body 11 are separated from each other comparatively so as to be in an opened state.

(Configuration: Relation Between Clip Main Body 11 of Clip 10 and Pressing Tube 31)

In the clip 10 with the above-described configuration, the first arm portion 12 and the second arm portion 13 are separated in the opposite direction X in the initial state. Therefore, as shown in FIG. 7, when the first locked portion 16 is projected to the proximal end side, the first locked portion 16 overlaps a portion of the edge 32a at the position P1 of the locking portion 32. That is, when the position of the first arm portion 12 with respect to the pressing tube 31 in the initial state in the opposite direction X and the orthogonal direction Z is maintained and the first arm portion 12 is moved toward the proximal end side with respect to the pressing tube 31, the first locked portion 16 comes into contact with the portion of the edge 32a at the position P1. The portion of the edge 32a at the position P1 comes into point contact with the first locked portion 16.

Likewise, when the first arm portion 12 is moved toward the proximal end side with respect to the pressing tube 31, the first locked portion 17 comes into contact with the portion of the edge 32a at the position P2. A part of the edge 32a at the position P2 comes into point contact with the first locked portion 17. A proximal end surface 16a of the first locked portion 16 comes into contact with the portion of the edge 32a at the position P1. A proximal end surface 17a of the first locked portion 17 comes into contact with the portion thereof at the position P2.

Positions of the edge 32a corresponding to the positions P1 and P2 in the orthogonal direction Z are indicated by positions Q1 and Q2 in FIG. 2.

When the second arm portion 13 integrally formed with the first arm portion 12 is moved toward the proximal end side with respect to the pressing tube 31, the second locked portions 21 and 22 come into contact with the locking portion 32 of the pressing tube 31, like the first locked portions 16 and 17 of the first arm portion 12.

(Configuration: Treatment Tool Body 40)

Next, the configuration of the treatment tool body 40 will be described.

As shown in FIGS. 1 and 2, the treatment tool body 40 includes the sheath tube 50, an insertion portion 60 and a manipulation portion 100. The insertion portion 60 is inserted inside the sheath tube 50 to be advanceable and retractable. The manipulation portion 100 is attached to the proximal end of the insertion portion 60.

The sheath tube 50 can be formed of, for example, a fluorine resin such as polytetrafluoroethylene (PTFE) or a resin material such as high-density polyethylene (HDPE).

(Configuration: Sheath Portion 61 of Treatment Tool Body 40)

The insertion portion 60 includes a sheath portion 61, a manipulation wire 62, and a connection member 63. The manipulation wire 62 is inserted into the sheath portion 61 so as to be advanceable and retractable. The connection member 63 is connected to the distal end of the manipulation wire 62. The connection member 63 is provided to be rotatable about an axis parallel to the opposite direction X with respect to the manipulation wire 62.

The sheath portion 61 includes a coil sheath 66 and a distal end member (stopper portion) 67 fixed to the distal end of the coil sheath 66. The coil sheath 66 is formed of stainless steel with a high compression resistance such as SUS301 of JIS (Japanese Industrial Standards).

A coil formed by densely winding a wire (not shown) in the axial line direction Y can be used as the coil sheath 66. The coil sheath 66 has flexibility and is strong against a compressive force in the axial line direction Y. The inner diameter of the coil sheath 66 is almost the same as the inner diameter of the helical spring 36.

The distal end member 67 is formed of stainless steel in a cylindrical shape. The inner diameter of the distal end member 67 is less than the inner diameter of the coil sheath 66. The outer diameter of the distal end member 67 is greater than that of the coil sheath 66 or the pressing tube 31. A concave portion 67a is formed on the outer circumferential surface of the proximal end of the distal end member 67 by reducing the outer diameter thereof. When the distal end of the coil sheath 66 engages with the concave portion 67a, the distal end member 67 and the coil sheath 66 are fixed together by laser welding or the like.

Thus, on the inner circumferential surface of the distal end of the sheath portion 61, a stepped portion 68 is formed in a connection portion of the coil sheath 66 and the distal end member 67 by reducing the inner diameter of the distal end member 67 provided more distal than the coil sheath 66 with respect to the coil sheath 66. The inner diameter of the distal end member 67 is formed so that the distal end member 67 does not engage with the first locked portions 16 and 17 and the second locked portions 21 and 22 when the clip 10 engages with the locking portion 32, as will be described below.

(Configuration: Distal End Member 67 of Treatment Tool Body 40)

A concave portion is formed over the entire inner circumferential surface of the distal end of the distal end member 67 and a support member 69 is disposed more distal than the concave portion. In this example, the support member 69 is formed in a cylindrical shape. The support member 69 has an inner diameter that is slightly greater than the outer diameter of the pressing tube 31 and has dimensions such that the proximal end of the pressing tube 31 can be accommodated therein. In the concave portion on the inner circumferential surface of the support member 69, a surface facing forward is a distal end support surface (distal end surface) 67b. The distal end support surface 67b can come into contact with the proximal end surface of the pressing tube 31. The clip 10 is disposed on the distal end side of the sheath portion 61. The support member 69 can support the outer circumferential surface of the pressing tube 31 coming into contact with the distal end support surface 67b.

In this configuration, shaking of the clip 10 with respect to the support member 69 can be suppressed to be as small as possible, and thus an inclination of the clip 10 with respect to the support member 69 can be allowed to some extent. Therefore, the endoscope treatment tool 1 can be inserted smoothly even into the bending shape of an endoscope channel or the like.

(Configuration: Manipulation Wire 62 of Treatment Tool Body 40)

The manipulation wire 62 is formed of a single line or a twisted line made of a metal. A loop portion 73 is provided at the distal end of the manipulation wire 62 via a diameter expansion portion 72. A linear member 74 (see FIG. 1) is formed by the manipulation wire 62 and the loop portion 73.

The diameter expansion portion 72 is formed of a metal or the like in a cylindrical shape. The outer diameter of the diameter expansion portion 72 is less than the inner diameter of the coil sheath 66 and is greater than the inner diameter of the distal end member 67. When the distal end surface of the diameter expansion portion 72 comes into contact with the stepped portion 68, the protrusion amount of the loop portion 73 with respect to the sheath portion 61 is regulated up to a length L2 (see FIG. 24). The length L2 is the maximum protrusion amount of the loop portion 73 allowed by the distal end member 67.

The loop portion 73 is formed by turning back a wire 73a. The wire 73a is turned back so that the turned portion is on the distal end side of the wire 73a. Both ends of the wire 73a are fixed to the diameter expansion portion 72 by brazing, resistance welding, or the like.

(Configuration: Connection Member 63 of Treatment Tool Body 40)

The connection member 63 includes a hook portion 77 at the distal end of a connection portion body 76, and a through hole 76a is formed at the proximal end of the connection portion body 76. An inclination surface 76b is formed on a surface facing the hook portion 77 in the connection portion body 76.

When the turned portion of the wire 73a of the loop portion 73 is inserted into the through hole 76a, the connection member 63 is connected to the loop portion 73 to be rotatable about an axis parallel to the opposite direction X (rotatable in an arrow direction D in FIG. 2).

The width of the connection member 63 is the outer diameter of the connection portion body 76 in a direction orthogonal to the central axial line C1 when the hook portion 77 is disposed on the distal end side of the connection portion body 76. The width of the connection member 63 is slightly less than the inner diameter of the helical spring 36, the inner diameter of the coil sheath 66, and the inner diameter of the distal end member 67. That is, the connection member 63 is not rotatable with respect to the loop portion 73 inside the pressing tube 31 and inside the sheath portion 61 when the hook portion 77 is disposed on the distal end side of the connection portion body 76. In other words, relative movement of the clip main body 11 and the hook portion 77 in a radial direction is regulated by the pressing tube 31 or the sheath portion 61.

The fact that "the connection member 63 is not rotatable with respect to the loop portion 73" mentioned here means that the connection member 63 is not rotatable with respect to the loop portion 73 until the engagement of the hook portion 77 and the middle portion 14 is released, as will be described below. Accordingly, the fact that "the connection member 63 is not rotatable with respect to the loop portion 73" does not literally mean that the connection member 63 is completely not rotatable with respect to the loop portion 73 even at a small angle.

By disposing the middle portion 14 between the hook portion 77 of the connection member 63 and the inclination surface 76b of the connection member 63, the hook portion 77 can engage with the middle portion 14. When the hook portion 77 is rotated with respect to the loop portion 73 in the direction D (see FIG. 2), the engagement of the hook portion 77 and the middle portion 14 is released. Thus, the connection member 63 is connected to be detachably mounted on the clip main body 11. The connection member 63 is located inside the pressing tube 31.

(Configuration: Manipulation Portion 100 of Treatment Tool Body 40)

As shown in FIG. 1, the manipulation portion 100 includes a manipulation portion main body 101, a slider 102, and a fracture mechanism 64. The manipulation portion main body 101 is installed on the proximal end of the coil sheath 66. The slider 102 is provided to be externally fitted to the manipulation portion main body 101 and to be slidable with respect to the manipulation portion main body 101 in the axial line direction Y. The fracture mechanism 64 is connected to the proximal end of the manipulation wire 62 and the slider 102.

The manipulation portion main body 101 is formed in a rod shape extending in the axial line direction Y. A finger hooking portion 101a is attached to the proximal end of the manipulation portion main body 101. On the proximal end side of the finger hooking portion 101a, a planar portion 101c is provided so that the manipulation portion 100 can be easily grasped with two hands (see FIG. 4). A slit 101b extending in the axial line direction Y is formed in the manipulation portion main body 101.

The slider 102 is formed in a cylindrical shape. On the outer circumferential surface of the slider 102, a concave portion 102a is formed around the circumference. A pair of flange portions 102b and 102c are formed in the slider 102 in the axial line direction Y so that the concave portion 102a is located between a pair of flange portions 102b and 102c. The pair of flange portions 102b and 102c have elliptical shapes when viewed in the axial line direction Y (see FIGS. 4 and 8). Thus, the slider 102 can be easily grasped. When the manipulation portion 100 of the endoscope treatment tool 1 is packed, space can be saved. As shown in FIG. 5, a groove 102e extending in the orthogonal direction Z is formed in a tube hole 102d of the slider 102.

When the slider 102 engages with the slit 101b of the manipulation portion main body 101, the movement range of the slider 102 with respect to the manipulation portion main body 101 in the axial line direction Y is regulated.

(Configuration: Fracture Mechanism 64 of Treatment Tool Body 40)

The fracture mechanism 64 is disposed inside the tube hole 102d of the slider 102, as shown in FIGS. 4 and 5. In other words, the fracture mechanism 64 is built in the manipulation portion 100.

Figure 9:
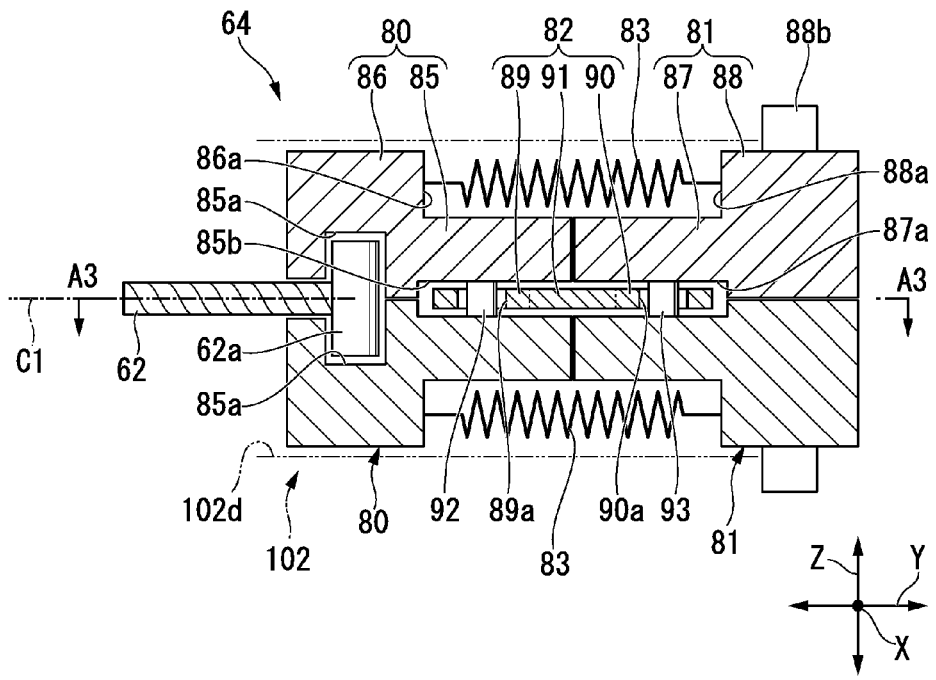
FIG. 9 is a top sectional view schematically showing a fracture mechanism of the endoscope treatment tool in FIG. 1.
Figure 10:
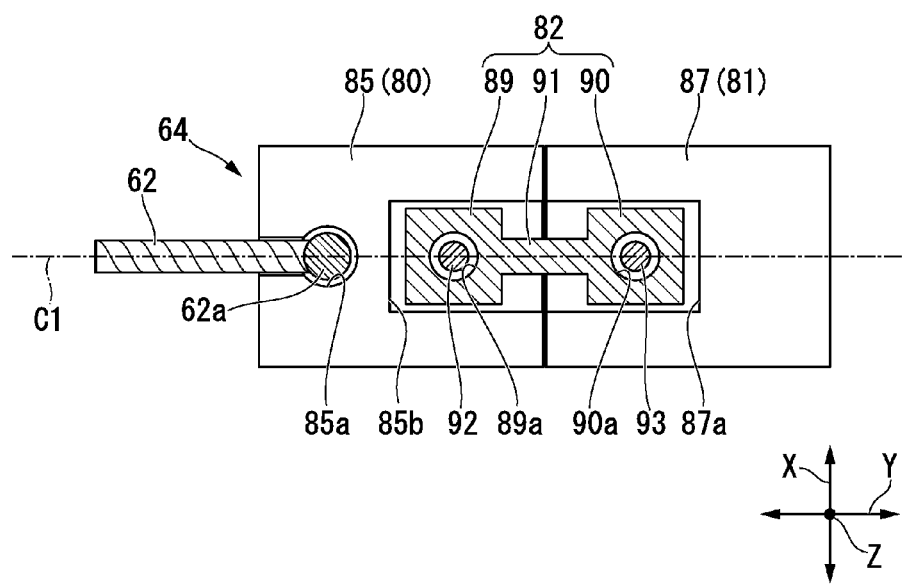
FIG. 10 is a diagram taken along the cutting line A3-A3 in FIG. 9.

As shown in FIGS. 9 and 10, the fracture mechanism 64 includes first support members 80, second support members 81, a fracturable member 82, and elastic members 83. The first support member 80 is connected to the proximal end of the manipulation wire 62. The second support member 81 is disposed on the proximal end side of the first support member 80. The fracturable member 82 and the elastic member 83 are connected to the first support member 80 and the second support member 81.

In this example, the fracture mechanism 64 includes a pair of first support members 80, a pair of second support members 81, and a pair of elastic members 83. The pair of the first support members 80, the pair of the second support members 81, and the pair of the elastic members 83 are disposed to be line-symmetric along the axial line C1 in a top view shown in FIG. 9.

As shown in FIGS. 9 and 10, the first support member 80 includes a support portion body 85 and a wall portion 86. The support portion body 85 is formed in a plate shape extending in the axial line direction Y. The wall portion 86 is erected in a direction which is the orthogonal direction Z from the distal end of the support portion body 85 and is a separation direction from the axial line C1. A groove 85a extending in the orthogonal direction Z is formed at the distal end of the surface of the support portion body 85 on the side of the axial line C1. An accommodation portion 85b is formed at the proximal end of the surface of the support portion body 85 on the side of the axial line C1. The first support member 80 is formed of a material such as a resin.

A wire fixing portion 62a is fixed to the proximal end of the manipulation wire 62 and has a larger diameter than the manipulation wire 62. The wire fixing portion 62a is formed integrally with the manipulation wire 62 and is interposed between both sides of the grooves 85a of the pair of the first support members 80 so as to engage with the pair of the first support members 80. Thus, the pair of the first support members 80 are connected to the proximal end of the manipulation wire 62.

(Configuration: Second Support Member 81 of Treatment Tool Body 40)

The second support members 81 are disposed to face the surfaces of the first support members 80 orthogonal to the axial line direction Y. Specifically, the second support member 81 includes a support portion body 87 and a wall portion 88. The support portion body 87 is formed in a plate shape extending in the axial line direction Y. The wall portion 88 is erected in an orthogonal direction Z which is orthogonal to the proximal end of the support portion body 87 and is a direction away from the axial line C1. An accommodation portion 87a is formed at the distal end of the surface of the support portion body 87 on the side of the axial line C1. A protrusion 88b is formed on a distal end surface of the wall portion 88 in the erection direction (the direction away from the axial line C1) in which the wall portion 88 is erected. The protrusion 88b engages with the groove 102e of the slider 102. The proximal end surface 86a of the wall portion 86 and the distal end surface 88a of the wall portion 88 face each other in the axial line direction Y.

(Configuration: Fracturable Member 82 of Treatment Tool Body 40)

The fracturable member 82 is formed of a metal such as stainless steel in a plate shape. The fracturable member 82 includes a first end portion 89, a second end portion 90, and a middle fracture portion 91. The first end portion 89 is connected to the support portion body 85 of the first support member 80. The second end portion 90 is connected to the support portion body 87 of the second support member 81. The middle fracture portion 91 is disposed between the first end portion 89 and the second end portion 90. The fracturable member 82 is configured such that the width of the middle fracture portion 91 is narrower than the width of the first end portion 89 and than the width of the second end portion 90.

A through hole 89a is formed in the first end portion 89. By inserting a pin 92 provided in the accommodation portion 85b of the support portion body 85 through the through hole 89a, the first end portion 89 is connected to the first support member 80. A through hole 90a is formed in the second end portion 90. By inserting a pin 93 provided in the accommodation portion 87a of the support portion body 87 through the through hole 90a, the second end portion 90 is connected to the second support member 81. Gaps are formed between the pin 92 and the through hole 89a and between the pin 93 and the through hole 90a. Even when the first support member 80 and the second support member 81 are connected via the fracturable member 82, the proximal end surface of the support portion body 85 can be extruded toward the distal end side on the distal end surface of the support portion body 87. Therefore, a load can be prevented from acting on the fracturable member 82 through manipulation of pushing of the manipulation wire 62 by the slider 102 to be described below. As a result, in the fracturable member 82, the fracture strength of the fracturable member 82 can be prevented from changing due to occurrence of work hardening or brittle cracking.

The fracture strength to a pulling force in the axial line direction Y is lower in the middle fracture portion 91 than in the first end portion 89 and than in the second end portion 90. The fracturable member 82 can be formed integrally by performing press working on a metal plate.

(Configuration: Strength of Fracturable Member 82 of Treatment Tool Body 40)

In the fracturable member 82, the middle fracture portion 91 is weaker than the first support member 80 and the second support member 81. The fracturable member 82 fractures due to the low fracture strength thereof in the axial line direction Y. The force which fractures the fracturable member 82 is higher (greater) than a force necessary to move the clip main body 11 accommodated in the pressing tube 31 toward the proximal end side with respect to the pressing tube 31 so as to make the clip main body 11 to enter an engagement state. Further, the fracture strength of the fracturable member 82 is lower than the fracture strength of the clip main body 11, the connection member 63, the loop portion 73, the diameter expansion portion 72, and the manipulation wire 62. In addition, the fracture strength of the fracturable member 82 is lower than the connection strength between the clip main body 11 and the connection member 63, between the connection member 63 and the loop portion 73, between the loop portion 73 and the diameter expansion portion 72, and between the diameter expansion portion 72 and the manipulation wire 62.

The fracture strength of the fracturable member 82 will be described as a specific numerical value. As will be described below, an amount of power (force) F1 necessary to pass over the clip 10 is in the range of about 20 N to about 50 N, the fracture strength of the fracturable member 82 fractures is set to about 100 N in consideration of a frictional force or the like inside the insertion portion 60.

(Configuration: Elastic Member 83 of Treatment Tool Body 40)

In the embodiment, the elastic member 83 is configured by a helical spring. The ends of the elastic member 83 are connected to the proximal end surface 86a of the wall portion 86 and the distal end surface 88a of the wall portion 88. The elastic member 83 is subjected to elastic deformation rather than plastic deformation even when the fracturable member 82 is drawn in the axial line direction Y by the fracture strength of the fracturable member 82.

The support members 80 and 81 are disposed inside the tube hole 102d of the slider 102, and thus the support members 80 and 81 are regulated to be moved only in the axial line direction Y with respect to the slider 102.

By engaging the protrusion 88b of the second support member 81 with the groove 102e of the slider 102, the second support member 81 is connected to the slider 102. The second support member 81 is integrated with the slider 102 and is slid in the axial line direction Y with respect to the manipulation portion main body 101. The first support member 80 is connected to the second support member 81 via the fracturable member 82 and the elastic member 83.

(Operation of Treatment Tool Body 40)

Next, an operation of the treatment tool body 40 will be described.

In the above-described configuration, the first support member 80, the second support member 81, and the fracturable member 82 can be integrally moved toward the proximal end side. That is, when the second support member 81 is pulled toward the proximal end side, the fracturable member 82 is moved toward the proximal end side, and the first support member 80 is accordingly moved toward the proximal end side.

The first support member 80 and the second support member 81 are connected to the manipulation wire 62. Therefore, when the second support member 81 is pulled toward the proximal end, the manipulation wire 62 can be pulled toward the proximal end side. Hence, by pulling the second support member 81 toward the proximal end side, the clip main body 11 is pulled back with respect to the pressing tube 31, the clip 10 is closed sequentially, and the locking portion 32 can be finally locked in the first locked portions 16 and 17 and the second locked portions 21 and 22.

When a manipulation is performed to move the second support members 81 toward the distal end side, the distal end surfaces of the support portion bodies 87 of the second support members 81 come into contact with the proximal end surfaces of the support portion bodies 85 of the first support members 80. Thus, when the second support members 81 are manipulated toward the distal end side, the first support members 80 are moved toward the distal end side and the manipulation wire 62 can therefore be moved toward the distal end side.

The outer diameters of the pins 92 and 93 of the first support members 80 and the second support members 81 are slightly less than the inner diameters of the through holes 89a and 90a of the fracturable member 82. Therefore, gaps are formed between the outer diameters of the pins 92 and 93 and the inner diameters of the through holes 89a and 90a. On the other hand, the gaps provided between the first support members 80 and the second support members 81 are configured to be less than the above gaps. Accordingly, even when the second support members 81 are moved toward the distal end side, the fracturable member 82 is configured so as not to move promptly toward the distal end side and a compressive force in the axial line direction Y does not occur in the fracturable member 82. Hence, deformation of the fracturable member 82 in which the fracture amount of power is changed, such as work hardening by deformation of the fracturable member 82, does not occur.

In the above-described configuration, the clip main body 11 can be moved toward the distal end side with respect to the pressing tube 31 when the second support members 81 are moved toward the distal end side. By sliding the slider 102 in the axial line direction Y with respect to the manipulation portion main body 101, the manipulation wire 62 can be manipulated to be advanced and retracted in the axial line direction Y.

(Action: Initial State)

Next, a technique used to ligate a target tissue with the clip 10 of the endoscope treatment tool 1 with the above-described configuration will be described.

Figure 11:
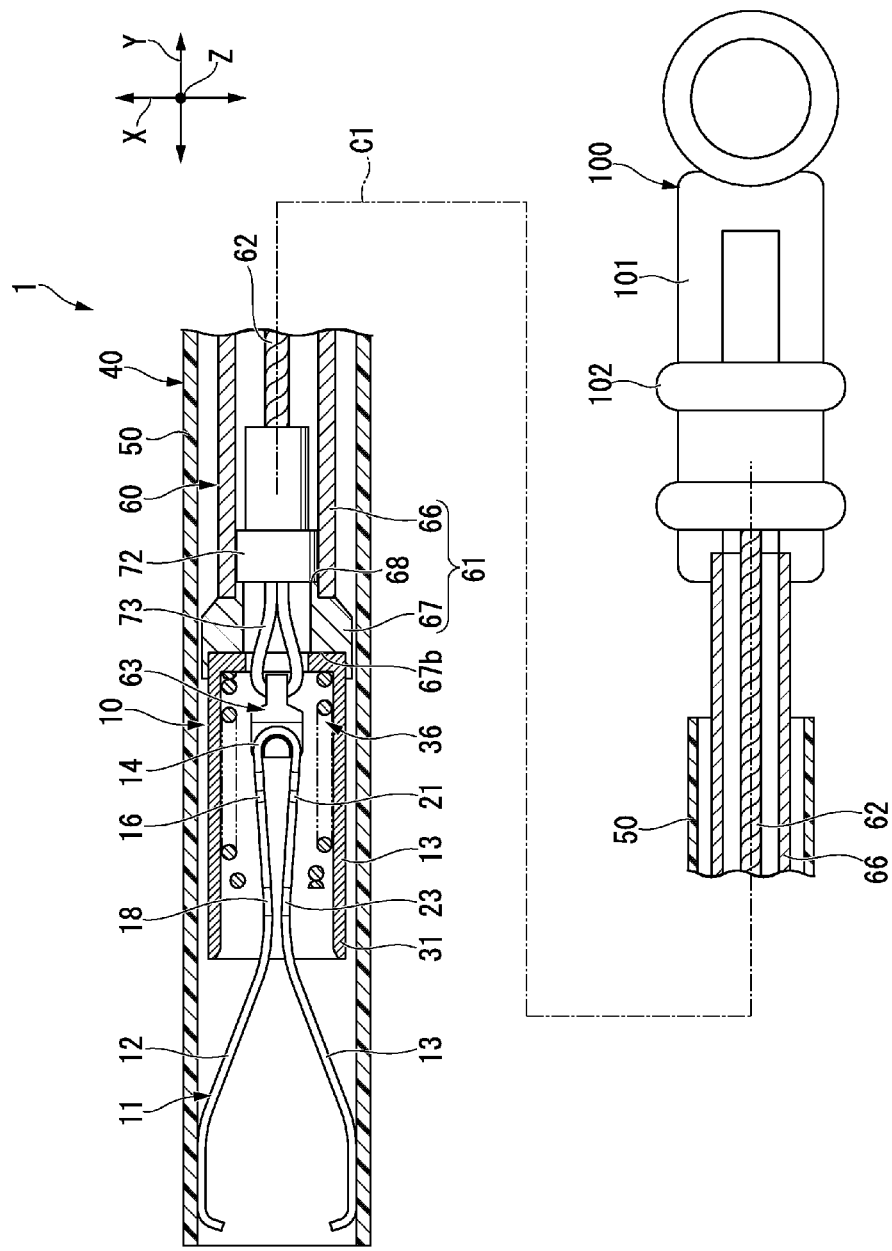
FIG. 11 is a schematic diagram showing a technique of using the endoscope treatment tool in FIG. 1.

When the endoscope treatment tool 1 is provided to a user who is an operator, as shown in FIG. 11, the sheath tube 50 is pushed to the insertion portion 60 so that the clip 10 installed in the treatment tool body 40 is hidden. The helical spring 36 of the clip 10 in the initial state is compressed in the axial line direction Y slightly more than in the natural state. Therefore, the proximal end surface of the pressing tube 31 comes into contact with the distal end support surface 67b. The distal end surface of the diameter expansion portion 72 comes into contact with the stepped portion 68 and the loop portion 73 protrudes up to the maximum protrusion amount from the distal end member 67.

Since the connection member 63 is disposed inside the pressing tube 31, the connection member 63 is not rotated with respect to the loop portion 73 and the engagement of the hook portion 77 and the middle portion 14 is maintained. At this time, the fracturable member 82 of the fracture mechanism 64 does not fracture.

When the endoscope treatment tool 1 is used, an endoscope insertion portion of an endoscope (not shown) is inserted into the body of a patient. The sheath tube 50 of the endoscope treatment tool 1 is inserted from the distal end of a channel of the endoscope and the sheath tube 50 protrudes from the distal end of the channel of the endoscope. When the sheath tube 50 is pulled back with respect to the insertion portion 60, the clip 10 protrudes from the distal end side of the sheath tube 50, as shown in FIG. 1. Thus, the arm portions 12 and 13 of the clip 10 enter an opened state shown in FIG. 1.

Figure 12:
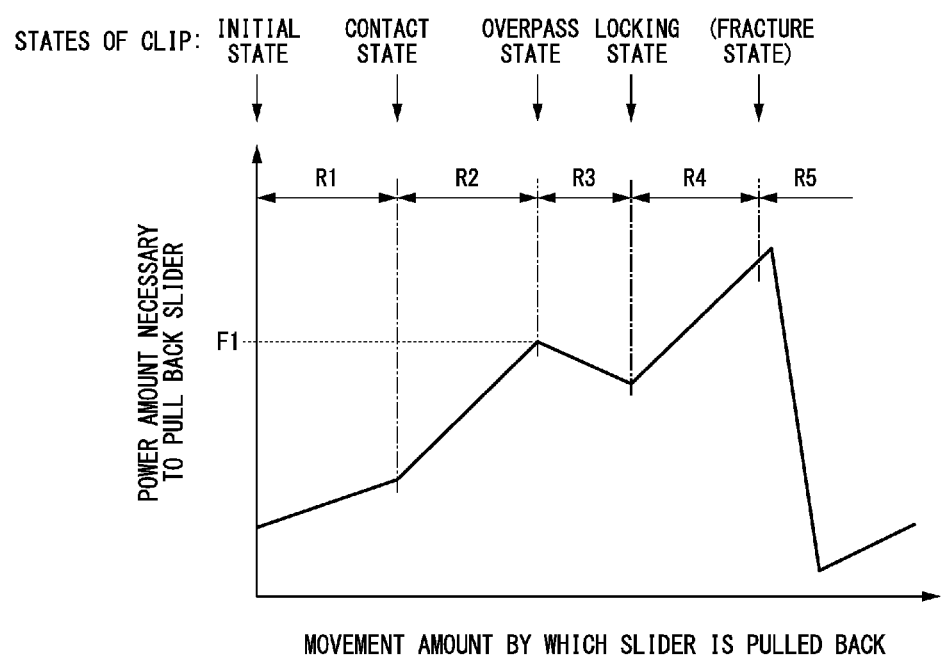
FIG. 12 is a schematic diagram showing an amount of power necessary to pull back a slider with respect to a movement amount by which the slider is pulled back in the endoscope treatment tool in FIG. 1.

FIG. 12 is a schematic diagram showing the amount of power necessary to pull back the slider with respect to the movement amount by which the slider is pulled back in the endoscope treatment tool. The slider 102 is moved (pulled back) toward the proximal end side with respect to the manipulation portion main body 101 from the initial state shown in FIG. 1. The clip 10 is configured such that the amount of power necessary to pull back the slider 102 changes with this movement, as shown in FIG. 12. In FIG. 12, a relative change in the amount of power necessary to pull back the slider in various states such as the initial state of the clip 10 are shown.

The state of the clip 10 is changed from the initial state to a contact state to an overpass state and then to a locking state as an operation of pulling back the slider 102. Hereinafter, the change in the amount of power and the change in the state of the clip 10 will be described in detail.

In the initial state, for example, the diameter expansion portion 72 comes into contact with the stepped portion 68 even when the slider 102 is erroneously moved (pushed) toward the distal end side with respect to the manipulation portion main body 101. Therefore, the proximal end surface of the pressing tube 31 comes into contact with the distal end support surface 67b, and the pressing tube 31 and the distal end support surface 67b are not separated over at least the depth of the support member 69 in the longitudinal direction.

Next, the clip 10 is turned toward the target tissue T (see FIG. 15) inside the body by performing a manipulation of curving a curving portion provided in the endoscope insertion portion while the inside of the body is examined with the endoscope. By pushing the endoscope treatment tool 1 in the endoscope, the arm portions 12 and 13 are pressed against the target tissue T.

When the user grasps the manipulation portion 100 and pulls back the slider 102, the first arm portion 12 and the second arm portion 13 are urged toward the inner circumferential surface of the distal end of the pressing tube 31. As a result, the first arm portion 12 is elastically deformed on the side of the second arm portion 13 and the second arm portion 13 is elastically deformed on the side of the first arm portion 12, and thus the distal end of the first arm portion 12 approaches the distal end of the second arm portion 13 (the arm portions 12 and 13 are closed). The helical spring 36 is gradually compressed in the axial line direction Y.

The amount of power by which the slider 102 is pulled back is transmitted to the fracturable member 82 via the second support member 81. Since small gaps are merely present between the pin 92 and the through hole 89a and between the pin 93 and the through hole 90a, the amount of power by which the slider 102 is pulled back is received by the fracturable member 82 rather than the elastic member 83.

(Action: Contact State from Initial State)

Figure 13:
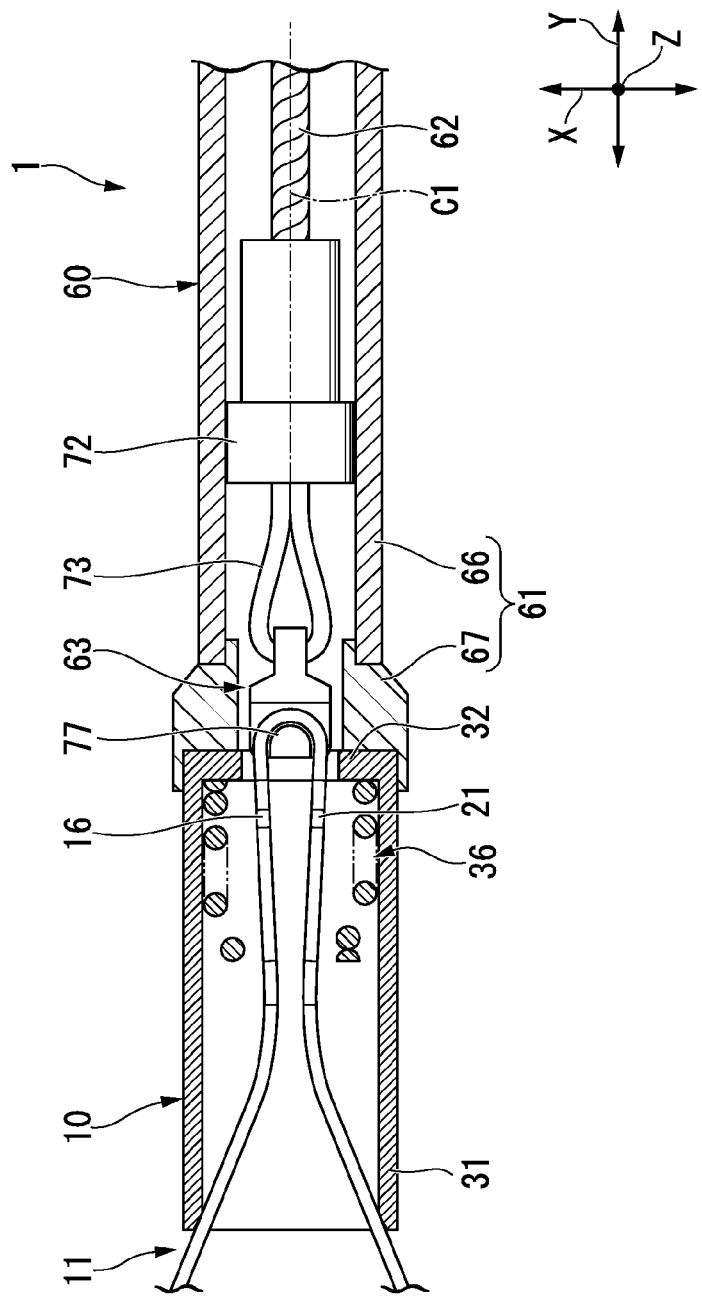
FIG. 13 is a side sectional view schematically showing the endoscope treatment tool when the clip unit in FIG. 1 is in a contact state.
Figure 14:
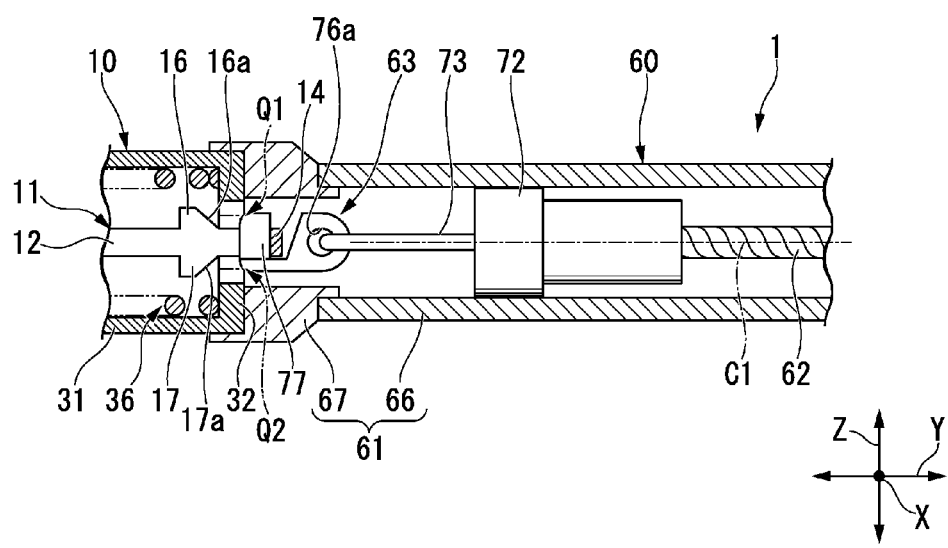
FIG. 14 is a top sectional view schematically showing the endoscope treatment tool when the clip unit in FIG. 1 is in the contact state.

When the slider 102 is pulled further back, as shown in FIGS. 7, 13, and 14, the first locked portions 16 and 17 and the second locked portions 21 and 22 enter the contact state with the locking portion 32 of the pressing tube 31. At this time, as shown in FIG. 7, the first locked portion 16 and the first locked portion 17 come into contact with the edge 32a of the pressing tube 31 at the position P1 and the position P2, respectively.

In a region R1 corresponding to the initial state to the contact state, as shown in FIG. 12, the amount of power necessary to pull back the slider 102 increases as the slider 102 is pulled back. The clip 10 is changed from the opened state to the closed state. Since the connection member 63 is disposed inside the pressing tube 31 or the sheath portion 61, the connection member 63 is not rotated with respect to the loop portion 73 and the engagement of the hook portion 77 and the middle portion 14 is maintained. Since the fracturable member 82 of the fracture mechanism 64 does not fracture, the amount of power by which the slider 102 is pulled back can be transmitted to the manipulation wire 62 via the fracturable member 82.

When the slider 102 is pushed, the proximal end surface of the support portion body 85 is extruded toward the distal end side by the distal end surface of the support portion body 87 of the fracture mechanism 64, so that the amount of power by which the slider 102 is pushed can be transmitted to the manipulation wire 62.

(Action: Overpass State from Contact State)

Proximal end surfaces 16a and 17a of the first locked portions 16 and 17 are formed to be inclined, as described above. The edge 32a of the locking portion 32 has a circular shape. Therefore, when the slider 102 is pulled further back, the first locked portion 16 receives a perpendicular force from the edge 32a in parallel to a normal line N orthogonal to a tangent line θ of the edge 32a at the position P1 at which the first locked portion 16 comes into contact with the edge 32a of the locking portion 32, when viewed in the axial line direction Y shown in FIG. 17. The perpendicular force moves the first locked portion 16 of the first arm portion 12 in the opposite direction X so that the first locked portion 16 becomes close to the second arm portion 13.

Figure 15:
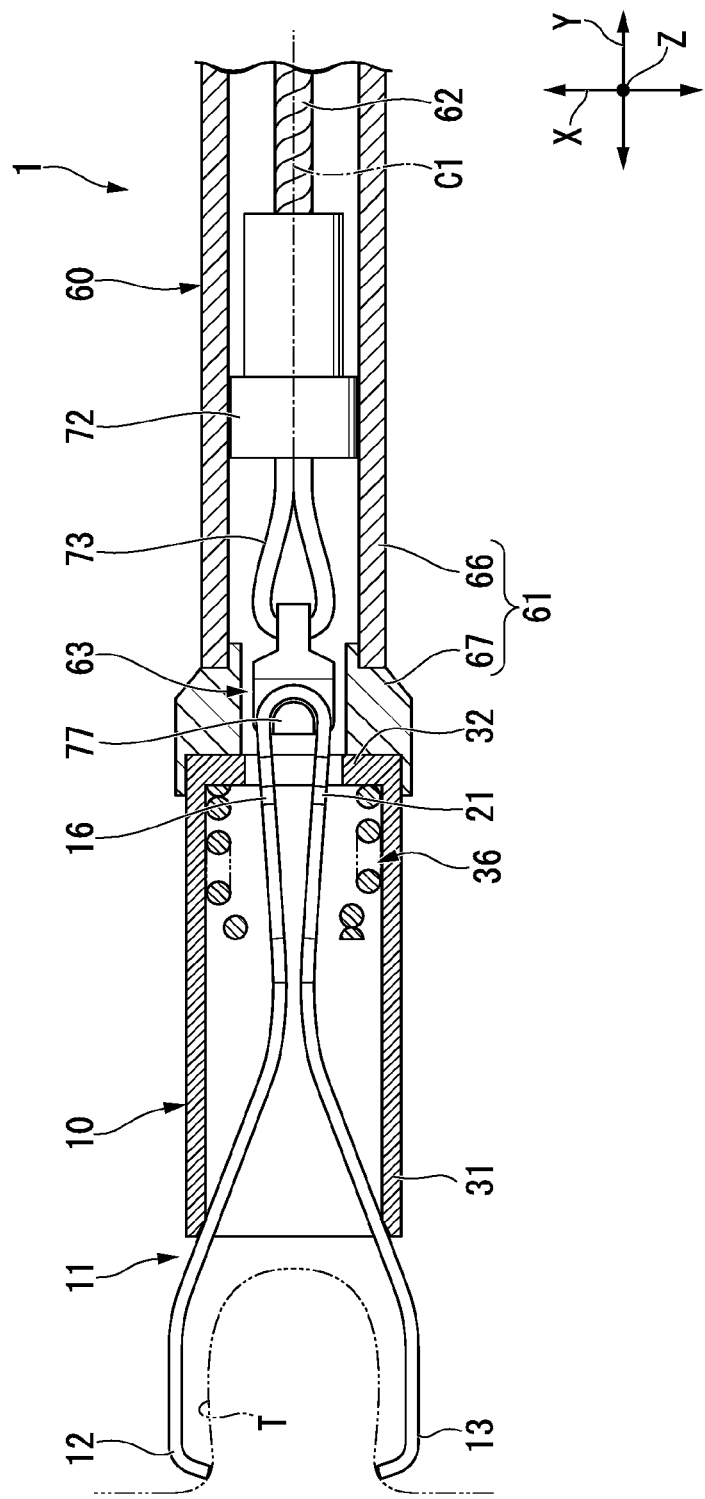
FIG. 15 is a side sectional view schematically showing the endoscope treatment tool when the clip unit in FIG. 1 is in an overpass state.
Figure 16:
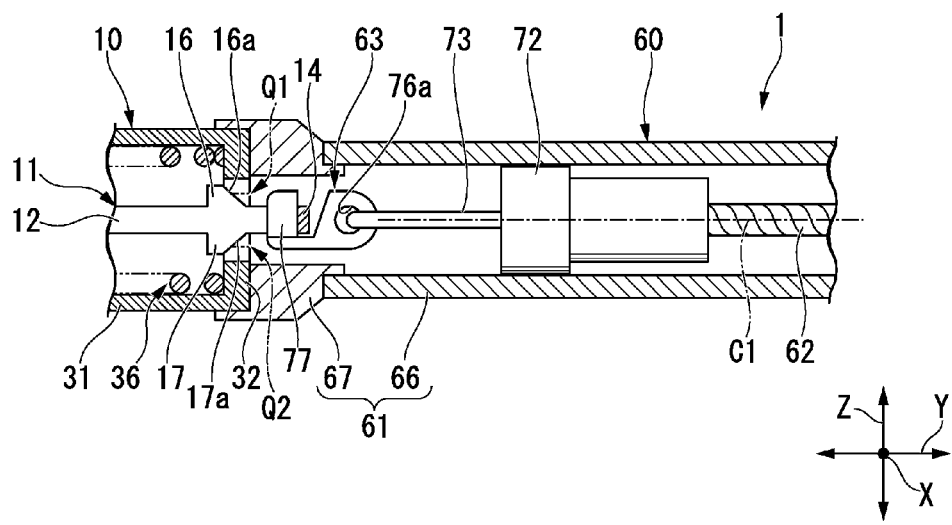
FIG. 16 is a top sectional view schematically showing the endoscope treatment tool when the clip unit in FIG. 1 is in the overpass state.
Figure 17:
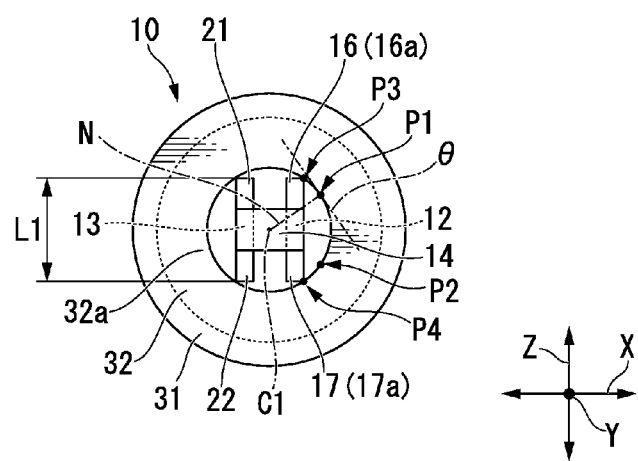
FIG. 17 is a schematic diagram of the clip unit in FIG. 1 in the overpass state when viewed from the proximal end side.

When the pullback manipulation continues, as shown in FIGS. 15 to 17, the first locked portions 16 and 17 come into point contact with the locking portion 32 and the edge 32a of the locking portion 32 with which the first locked portion 16 comes into contact moves from the position P1 to a position P3. Simultaneously, the edge 32a of the locking portion 32 with which the first locked portion 17 comes into contact moves from the position P2 to a position P4. FIGS. 15 to 17 illustrate the overpass state in which the distal end of the proximal end surface 16a of the first locked portion 16 and the distal end of the proximal end surface 17a of the first locked portion 17 come into contact with the edge 32a of the locking portion 32.

Likewise, the second arm portion 13 receives the perpendicular force from the edge 32a of the locking portion 32 and moves in the opposite direction X to become close to the first arm portion 12. At this time, the middle portion 14 is elastically deformed so that both ends of the middle portion 14 move toward the side of the axial line C1.

By rotating the manipulation wire 62 with respect to the sheath portion 61 in the initial state, the direction of the clip 10 can be adjusted. At this time, the clip main body 11 is considered to be rotated about the axial line C1 with respect to the pressing tube 31. However, since the edge 32a of the locking portion 32 is formed in the circular shape coaxial with the pressing tube 31, the locking state of the locking portion 32, the first locked portions 16 and 17, and the second locked portions 21 and 22 is maintained satisfactorily.

In a region R2 corresponding to the contact state to the overpass state, as shown in FIG. 12, an increasing rate of the amount of power increasing necessary to pull back the slider 102 per unit movement amount by which the slider 102 is pulled back is greater than in the above-described region R1. In other words, while the change of the amount of power characteristic in which the gradient is relatively gentle is shown in the region R1, a change of the amount of power characteristic in which the gradient is relatively sharp is shown in the region R2 in which the first locked portions 16 and 17 and the second locked portions 21 and 22 come into contact with the locking portion 32.

That is, the user who pulls back the slider 102 feels that the slider 102 is abruptly heavier in the region R1 than in the region R2 when the user pulls back the slider 102. Thus, the user can easily recognize whether a state in which the user is currently pulling back the slider 102 is in the region R1 or the region R2, in other words, the user can easily recognize whether the slider 102 is being pulled beyond the contact state.

In the region R2, the closed state of the clip 10 is maintained. Since the connection member 63 is disposed inside the sheath portion 61, the engagement of the hook portion 77 and the middle portion 14 is maintained. The fracturable member 82 of the fracture mechanism 64 does not fracture. For example, an amount of power F1 necessary to cause the clip 10 to enter the overpass state, as shown in FIG. 12, is in the range of about 20 N to about 50 N (newtons).

As shown in FIG. 17, in the overpass state, a distance between the positions P3 and P4 of the edge 32a is the same as the length L1 of the first locked portions 16 and 17 described above.

(Action: Re-Gripping)

The clip 10 is elastically deformed. Therefore, when the slider 102 is pushed while the clip 10 is in any state in the regions R1 and R2, the compressed helical spring 36 is stretched. When the pressing tube 31 comes into contact with the distal end support surface 67b, the clip main body 11 is moved toward the distal end side with respect to the pressing tube 31 and the clip 10 enters the initial state shown in FIG. 1. For example, through the manipulation of the curving of the curving portion, the clip 10 is turned toward another target tissue T. Thereafter, by performing the steps in the above-described order, the target tissue T can be re-gripped with the clip 10.

(Action: Locking State from Overpass State)

When the slider 102 is pulled further back from the overpass state, the positions of the first arm portion 12 and the second arm portion 13 with respect to the pressing tube 31 in the opposite direction X and the orthogonal direction Z are maintained. In this state, the first arm portion 12 provided with the first locked portions 16 and 17 and the second arm portion 13 provided with the second locked portions 21 and 22 are inserted inside the locking portion 32. Then, the first locked portions 16 and 17 and the second locked portions 21 and 22 are moved toward the proximal end side beyond the locking portion 32.

Figure 18:
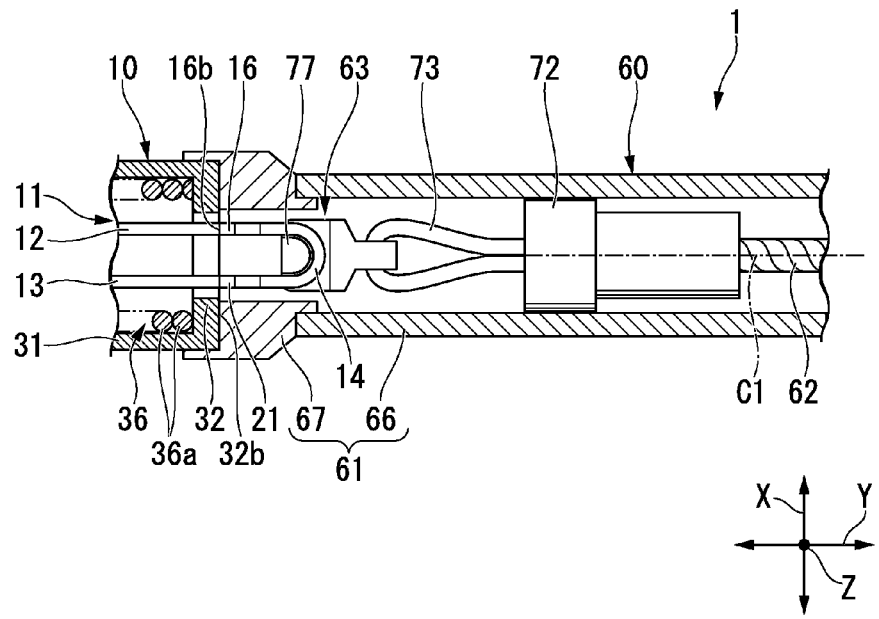
FIG. 18 is side sectional view schematically showing the endoscope treatment tool when the clip unit in FIG. 1 is in a locking state.
Figure 19:
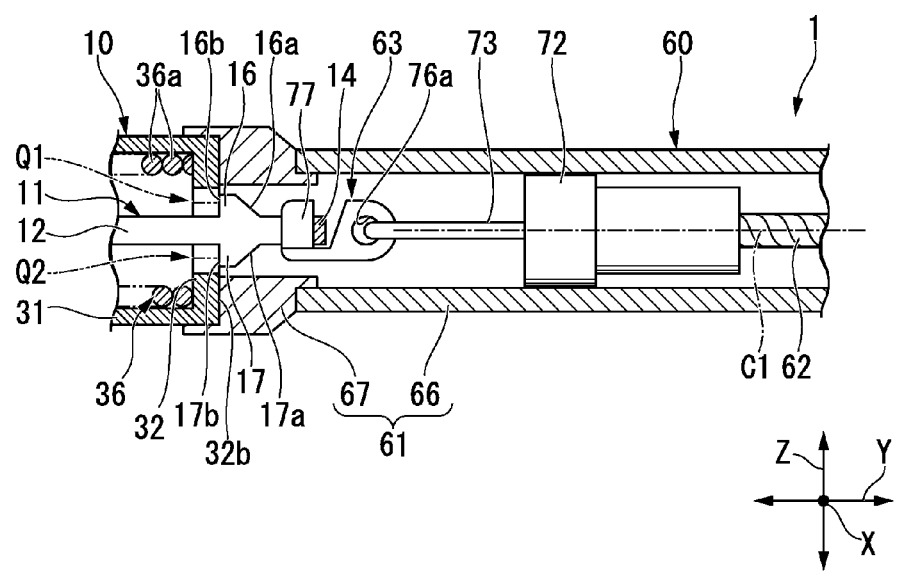
FIG. 19 is top sectional view schematically showing the endoscope treatment tool when the clip unit in FIG. 1 is in the locking state.
Figure 20:
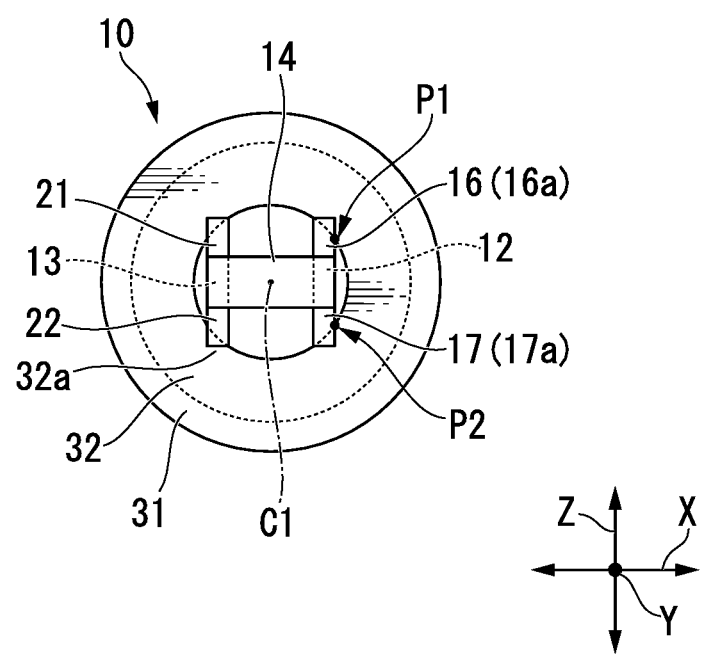
FIG. 20 is a schematic diagram showing the clip unit in FIG. 1 in the locking state when viewed from the proximal end side.

At this time, the arm portions 12 and 13 and the middle portion 14 are not urged from the locking portion 32. Therefore, as shown in FIGS. 18 to 20, the proximal end side of the first arm portion 12 and the proximal end side of the second arm portion 13 are moved in the opposite direction X by the elastic force of the middle portion 14 to be separated from each other. When a force for moving the clip main body 11 toward the proximal end side of the pressing tube 31 is released, the distal end surfaces 16b and 17b of the first locked portions 16 and 17 enter the locking state in which the distal end surfaces 16b and 17b are locked with the proximal end surface 32b of the locking portion 32 on the distal end side of the proximal end surface 32b.

In a region R3 corresponding to the overpass state to the locking state, as shown in FIG. 12, a part of the elastic deformation of the arm portions 12 and 13 and the middle portion 14 is released. Thus, the amount of power necessary to pull back the slider 102 gradually decreases as the slider 102 is pulled back. In the region R3, the closed state of the clip 10 is maintained. Since the connection member 63 is disposed inside the sheath portion 61, the engagement of the hook portion 77 and the middle portion 14 is maintained. The fracturable member 82 of the fracture mechanism 64 does not fracture.

When the clip 10 enters the locking state, as shown in FIGS. 18 and 19, the wires 36a of the helical spring 36 compressed in the axial line direction Y enter a close coiling state in which the wires 36a adjacent in the axial line direction Y are almost appressed. When the clip 10 enters the locking state, the distal end surfaces 16b and 17b of the first locked portions 16 and 17 lock with the proximal end surface 32b of the locking portion 32. Therefore, the movement of the clip main body 11 with respect to the pressing tube 31 toward the distal end side is regulated. That is, a state in which the clip 10 ligates the target tissue T is maintained and the state of the clip does not return to the initial state in which the arm portions 12 and 13 enter the opened state. The clip 10 is fixed in the state in which the arm portions 12 and 13 are closed. In the clip 10, the middle portion 14 protrudes on the proximal end side with respect to the pressing tube 31.

When the first locked portions 16 and 17 and the second locked portions 21 and 22 are moved toward the proximal end side beyond the locking portion 32, the first locked portions 16 and 17 and the second locked portions 21 and 22 may pass over the locking portion 32 by scraping against the locking portion 32 or deforming the locking portion 32. In this case, in order to prevent excessive breakage of the locking portion 32, it is desirable to perform a chamfering process or the like on portions in which the first locked portions 16 and 17 and the second locked portions 21 and 22 come into contact with the locking portion 32.

(Action: Immediately Before Fracture State)

Since the helical spring 36 is in the close coiling state, the clip main body 11 may not be moved toward the proximal end side with respect to the pressing tube 31 even if the slider 102 is pulled further back. The locking state of the clip 10 is maintained and not changed. However, when the slider 102 is pulled back, a tensile force acting on the fracturable member 82, the manipulation wire 62, or the like gradually increases. In a region R4 shown in FIG. 12, i.e., the region R4 corresponding to the locking state to a state immediately before a fracture state of the fracture mechanism 64 to be described below, as shown in FIG. 12, the closed state of the clip 10 is maintained. Since the connection member 63 is disposed inside the sheath portion 61, the engagement of the hook portion 77 and the middle portion 14 is maintained. The fracturable member 82 of the fracture mechanism 64 does not fracture.

(Action: Fracture State)

Figure 21:
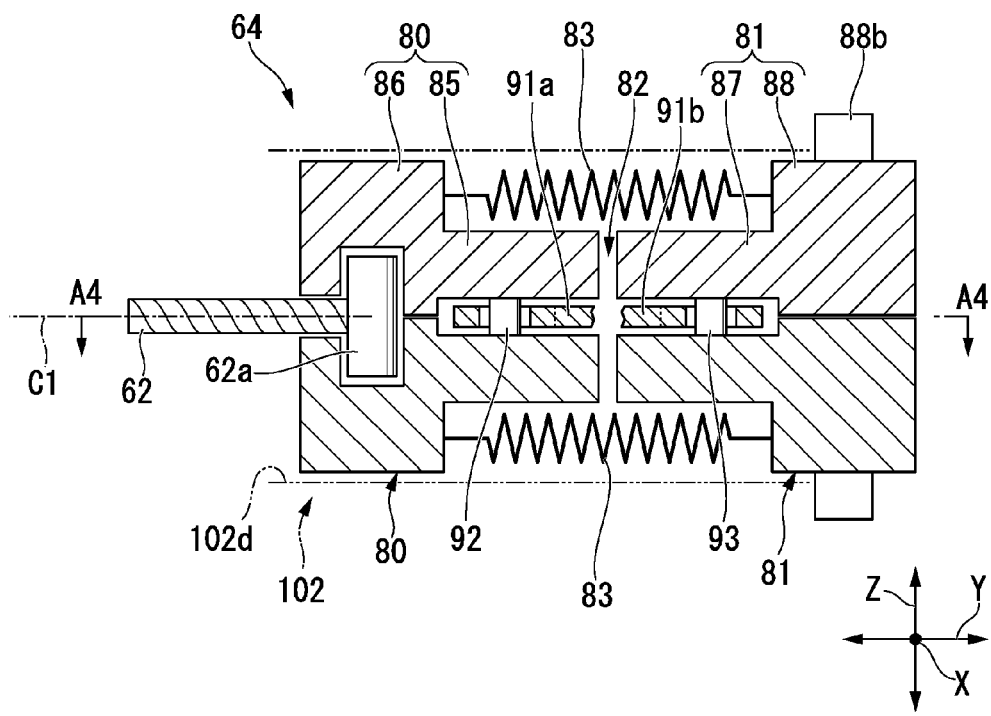
FIG. 21 is a top sectional view schematically showing the fracture mechanism in a fracture state when a technique using the endoscope treatment tool showing in FIG. 1 is performed.
Figure 22:
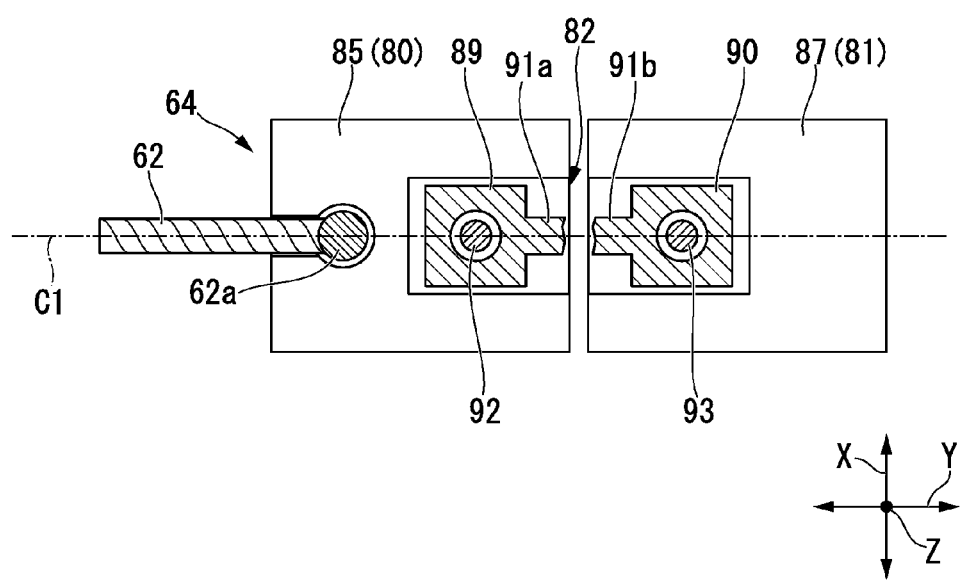
FIG. 22 is a view along the cutting line A4-A4 in FIG. 21.

The slider 102 is pulled further back, a manipulation amount of power of the slider 102 reaches a value equal to or greater than a predetermined value, and the tensile force acting on the fracturable member 82 exceeds the fracture strength of the fracturable member 82. At this time, as shown in FIGS. 21 and 22, the middle fracture portion 91 of the fracturable member 82 in the fracture mechanism 64 fractures and the middle fracture portion 91 is separated into fracture pieces 91a and 91b. Thus, the fracture mechanism 64 enters the fracture state in which the fracturable member 82 fractures.

Due to a fracture impact, the fracture piece 91a and the first support member 80 each attempt to fly out toward the distal end side. However, the movement toward the distal end side is regulated since the first support member 80 and the second support member 81 are connected by the elastic member 83. The clip 10 does not deviate from the support member 69. After the fracturable member 82 fractures, the connection state between the first support member 80 and the second support member 81 is maintained by the elastic member 83.

The fracture impact of the middle fracture portion 91 is transmitted to the user grasping the manipulation portion 100. That is, the fracture mechanism 64 causes the user to recognize that the clip 10 is fixed in the closed state when the fracturable member 82 fractures. Since the fracture mechanism 64 is provided in the manipulation portion 100, the user can more reliably recognize this impact.

When the user feels the transmitted impact, the user can recognize that the clip 10 has entered the locking state and the ligation state of the target tissue T is maintained. Even when the user pulls the slider 102 further back and brings the slider 102 into contact with the proximal end of the slit 101b of the manipulation portion main body 101, the user can recognize that the clip 10 has entered the locking state.

The first support member 80 and the second support member 81 are connected by the elastic member 83. Therefore, when the slider 102 is pulled further back, the elastic member 83 is stretched. Since the clip 10 is in the locking state, the manipulation wire 62 is not moved toward the proximal end side.

A region R5 shown in FIG. 12 includes the fracture state and a state in which the slider 102 is pulled further back than the clip is in the fracture state. In the region R5 shown in FIG. 12, the fracturable member 82 fractures and then the elastic member 83 is stretched, and thus the amount of power necessary to pull back the slider 102 temporarily decreases and then increases as the slider 102 is pulled back. In the region R5, the closed state of the clip 10 is maintained.

Since the connection member 63 is disposed inside the sheath portion 61, the engagement of the hook portion 77 and the middle portion 14 is maintained. The fracturable member 82 of the fracture mechanism 64 fractures.
(Action: Separation of Clip 10)

Thereafter, the clip 10 is separated from the treatment tool body 40.

Figure 23:
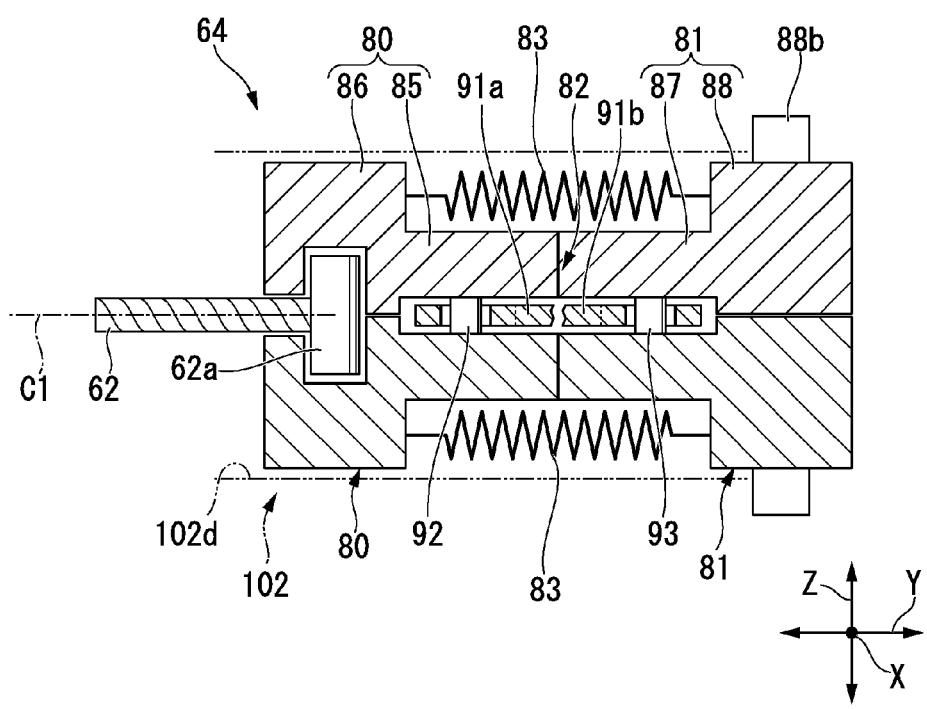
FIG. 23 is a schematic diagram showing the technique of using the endoscope treatment tool in FIG. 1.
Figure 24:
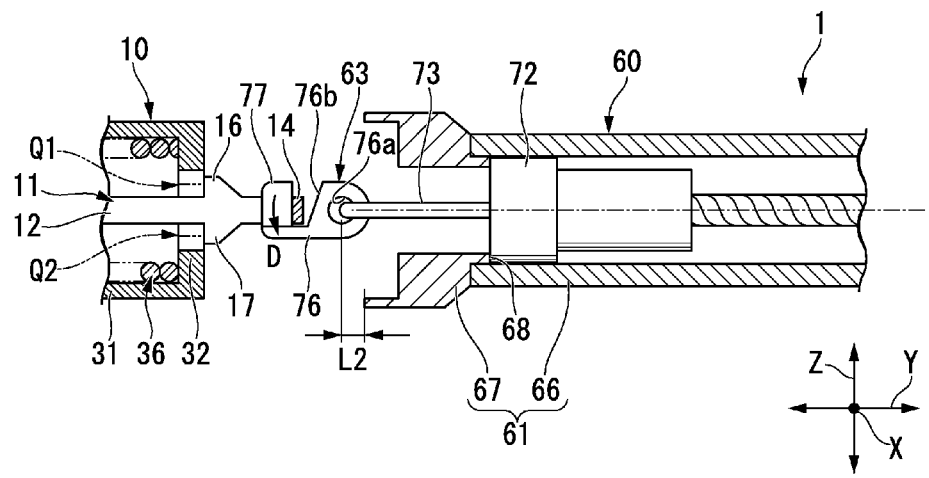
FIG. 24 is a schematic diagram showing the technique of using the endoscope treatment tool in FIG. 1.

The order in which the clip 10 is separated from the treatment tool body 40 is specifically as follows. That is, when the slider 102 is pushed, as shown in FIG. 23, the proximal end surface of the first support member 80 is extruded to the distal end surface of the second support member 81 and the manipulation wire 62 is moved toward the distal end side with respect to the coil sheath 66. As shown in FIG. 24, the distal end surface of the diameter expansion portion 72 comes into contact with the stepped portion 68 and the loop portion 73 protrudes up to the length L2 which is the maximum protrusion amount with respect to the distal end member 67.

Figure 25:
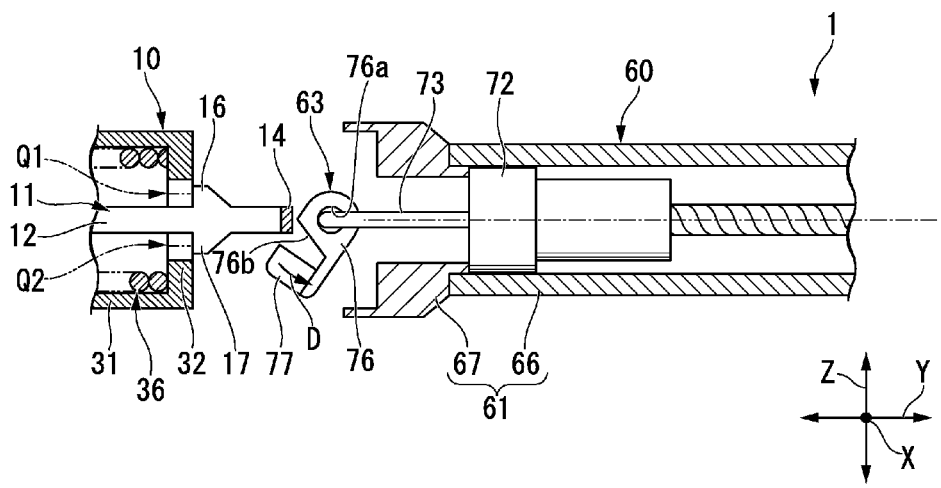
FIG. 25 is a schematic diagram showing the technique of using the endoscope treatment tool in FIG. 1.

When the connection member 63 protrudes on the distal end side with respect to the distal end member 67, the clip main body 11 and the pressing tube 31 are integrally moved toward the distal end side. Since the connection member 63 is located out of the pressing tube 31, the connection member 63 can be rotated with respect to the loop portion 73. When the slider 102 is pushed and the manipulation wire 62 is moved toward the distal end side, the inclination surface 76b of the connection member 63 comes into contact with the proximal end surface of the middle portion 14 of the clip 10 ligating the target tissue T. As shown in FIG. 25, the hook portion 77 is guided to the inclination surface 76b and is rotated in the direction D along with the connection portion body 76, and thus the engagement of the hook portion 77 and the middle portion 14 is released. Thus, the clip 10 ligating the target tissue T is maintained inside the body.

That is, the closed state of the clip 10 is maintained between the state indicated by the region R5 and a state in which the slider 102 is pushed and the connection member 63 protrudes toward the distal end side with respect to the distal end member 67, as shown in FIG. 24. The engagement of the hook portion 77 and the middle portion 14 can be released. The fracturable member 82 of the fracture mechanism 64 fractures.
(Action: Final Treatment of Technique)

The slider 102 is pulled back and the connection member 63 is accommodated inside the sheath portion 61.

The endoscope treatment tool 1 is extracted from the channel of the endoscope. The endoscope insertion portion of the endoscope is extracted from the body of the patient. Thereafter, necessary treatment is performed and a series of operations of the technique ends.
(Advantages)

In the endoscope treatment tool 1 according to the present embodiment, in the initial state of the clip 10, the clip main body 11 is accommodated in the pressing tube 31 such that the first locked portions 16, 17 and the second locked portions 21, 22 are disposed more distal than the locking portion 32. In the initial state of the clip 10, when the loop portion 73 is protruded to a position with the maximum protrusion amount allowed by the distal end member 67, the connection member 63 is disposed inside the pressing tube 31 such that release of the connection structure between the clip 10 and the connection member 63 is prevented. On the other hand, in the engagement state of the clip 10, the clip main body 11 is moved such that the first locked portions 16, 17 and the second locked portions 21, 22 are moved toward the proximal end side beyond the locking portion 32. In the engagement state of the clip 10, when the loop portion 73 is protruded to a position corresponding to the maximum protrusion amount allowed by the distal end member 67, the connection member 63 is disposed outside the pressing tube 31. Therefore, it is possible to release the connection structure between the clip 10 and the connection member 63.

In the endoscope treatment tool according to the present embodiment, the connection member 63 is separated from the clip 10 by protruding the loop portion 73 to the position with the maximum protrusion amount after the clip 10 is switched from the initial state to the engagement state. Therefore, it is possible to stabilize the state in which the connection member 63, that is, the treatment tool body 40 is separated from the clip 10. In the endoscope treatment tool according to the present embodiment, it is possible to switch between a state in which the clip 10 and the connection member 63 is connected and a state in which the clip 10 and the connection member 63 is separated. Therefore, it is easy to release the connection structure between the clip 10 and the connections member 63.

In the endoscope treatment tool 1 according to the present embodiment, the stepped portion 68 is formed in the sheath portion 61, and the diameter expansion portion 72 is formed in the linear member 74. When the manipulation wire 62 is inserted, the stepping portion 68 engages with the diameter expansion portion 72. Therefore, it is possible to regulate the protrusion length of the clip 10 from the sheath portion 61 toward the distal side. Moreover, the sheath portion 61 includes the support member 69 such that when the clip 10 is in the initial state, the proximal end of the pressing tube 31 is accommodated in the support member 69 to suppress the shaking of the clip 10 with respect to the support member 69.

The embodiment of the present invention has been described in detail above with reference to the drawings, but the specific configuration is not limited to the embodiment. Changes and the like in the configuration are included within the scope of the present invention without departing from the gist of the present invention.

For example, in the foregoing embodiment, the support member 69 is formed in a cylindrical shape. However, the configuration of the support member 69 is not limited to the foregoing embodiment. For example, the support member 69 may be formed by two or more members which are separated from each other and are disposed around the axial line C1, while angles between each of the members and the axial line C1 are equal. In such a situation, the distance between each of the members and the axial line C1 is determined to be slightly larger than half of the outer diameter of the pressing tube 31.

In the endoscope treatment tool 1 according to the foregoing embodiment, the sheath tube 50 may not be included. This is because there is no problem in some cases even when the sheath tube 50 is not provided at the time of insertion into the channel of the endoscope since the outer diameter is small at the time of the opened state of the clip 10.

In the endoscope treatment tool 1 according to the foregoing embodiment, the manipulation portion 100 may not be included. This is because the clip 10 can be manipulated even in the advancement and retraction of the second support member 81 with respect to the coil sheath 66.

In the foregoing embodiment, the case in which the stepped portion 68 is formed in the sheath portion 61 and the diameter expansion portion 72 is provided in the linear member 74 has been described. However, when an insertion amount of the manipulation wire 62 with respect to the sheath portion 61 can be easily known, e.g., when an indicator is provided in the manipulation wire 62, the stepped portion 68 or the diameter expansion portion 72 may not be provided.

In the foregoing embodiment, for example, when a force by which the helical spring 36 of the clip 10 is compressed by the treatment tool body 40 in the initial state is large, the pressing tube 31 is rarely shaken with respect to the distal end member 67. Therefore, the support member 69 may not be provided in the distal end member 67.

In the embodiment, the fracture mechanism 64 includes a pair of first support members 80, a pair of second support members 81, and a pair of elastic members 83. However, the fracture mechanism 64 may be configured to include at least only one member among the first support members 80, the second support members 81, and the elastic members 83.

While preferred embodiments of the invention have been described and illustrated above, it should be understood that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims.

What is claimed is:

1. An endoscope treatment tool comprising:
   a clip main body which includes a pair of arm portions, each arm portion of the pair of the arm portions extending from a proximal end to a distal end and facing each other;
   a pressing tube through which the clip main body is inserted and is provided to make the distal ends of the pair of the arm portions approach each other;
   a locking portion which is disposed on an inner circumferential surface of a proximal end of the pressing tube;
   a locked portion which is disposed on a proximal end side of the clip main body;
   a sheath portion, the clip main body being disposed distally relative to the sheath portion;
   a linear member connected to the clip main body and inserted through the sheath portion to be capable of being advanced and retracted;
   a stopper portion which is disposed at a distal end of the sheath portion, the stopper portion being configured to restrict an advancement of the linear member toward a distal end side of the sheath portion; and
   a connection member which is disposed at a distal end of the linear member, the connection member being configured to connect the linear member and the clip main body,
   wherein the connection member is configured to prevent an engagement of the linear member with the clip main body from being released, when the linear member is advanced to a position regulated by engaging the linear member with the stopper portion, in a state in which the clip main body is accommodated in the pressing tube such that the locked portion is disposed more distally than the locking portion, and
   wherein the connection member is configured to release the engagement of the linear member with the clip main body by advancing the linear member to a position regulated by engaging the linear member with the stopper portion, in a state in which the locked portion is disposed more proximally than the locking portion such that a movement of the clip main body is restricted.

2. The endoscope treatment tool according to claim 1, wherein
   the connection member includes a hook portion which engages with the clip main body, and
   in a state in which the connection member is positioned inside the pressing tube, a relative movement in a radial direction between the clip main body and the hook portion is regulated by the pressing tube such that release of the engagement between the hook portion and the clip main body is prevented.

3. The endoscope treatment tool according to claim 2, wherein
   the sheath portion includes a support member which is capable of accommodating the proximal end of the pressing tube in a distal side of the support member, and
   at least part of a proximal part of the pressing tube is accommodated in the support member when the linear member is advanced to a first position that is restricted by the stopper portion, in a state in which the clip main body is accommodated in the pressing tube such that the locked portion is positioned more distal than the locking portion.

4. The endoscope treatment tool according to claim 3, wherein
   the stopper portion is disposed at the distal end side of the sheath portion.

5. The endoscope treatment tool according to claim 4, wherein
   the connection member is connected to a proximal end of the clip main body, and
   in a state in which the clip main body is moved such that the locked portion is positioned more proximal than the locking portion, the proximal end of the clip main body is protruded from a proximal end portion of the pressing tube such that the connection member is positioned outside the pressing tube to release the connection between the clip main body and the connection member.

6. The endoscope treatment tool according to claim 5, wherein
   the hook portion is connected to the linear member and is capable of rotating around an axial which is perpendicular to a longitudinal axis of the linear member.

7. The endoscope treatment tool according to claim 1, further comprising:
   a stepped portion which is disposed at the stopper portion and has an inner diameter smaller than an inner diameter of the sheath portion; and
   a diameter expansion portion which is disposed at the linear member and is disposed at a more proximal side of the sheath portion than the stepped portion, the diameter expansion portion having an outer diameter smaller than the inner diameter of the sheath portion and larger than the inner diameter of the stepped portion,
   wherein the stopper portion restricts the advancement of the linear member when the linear member is advanced to a position at which the diameter expansion portion contacts with the stepped portion.

* * * * *